US008301390B2

(12) United States Patent
Sastry et al.

(10) Patent No.: US 8,301,390 B2
(45) Date of Patent: Oct. 30, 2012

(54) QUANTUM CHEMISTRY SIMULATIONS USING OPTIMIZATION METHODS

(75) Inventors: Kumara Sastry, Hillsboro, OR (US); Duane D. Johnson, Champaign, IL (US); Alexis L. Thompson, Champaign, IL (US); Todd J. Martinez, Champaign, IL (US); David E. Goldberg, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1178 days.

(21) Appl. No.: 12/012,502

(22) Filed: Jan. 31, 2008

(65) Prior Publication Data

US 2008/0312895 A1 Dec. 18, 2008

Related U.S. Application Data

(60) Provisional application No. 60/898,952, filed on Jan. 31, 2007.

(51) Int. Cl.
*G06F 7/00* (2006.01)
(52) U.S. Cl. ............... 702/19; 702/20; 703/11; 707/700
(58) Field of Classification Search ........................ None
See application file for complete search history.

(56) References Cited

U.S. PATENT DOCUMENTS

2006/0040322 A1* 2/2006 Archetti et al. ................ 435/7.1

OTHER PUBLICATIONS

Alder & Wainwright, "Studies in Molecular Dynamics. I. General Method." Journal of Chemical Physics, 32, pp. 459-466, 1959.
Alder & Wainwright, "Studied in Molecular Dynamics. II. Behaviour of a Small Number of Elastic Spheres." Journal of Chemical Physics, 33, pp. 1439-1451, 1960.
Babovic & Keijzer, "Genetic Programming as a Model Induction Engine." Journal of Hydroinformatics, 2(1), pp. 35-60, 2000.
Barkema & Mousseau, "Event-based Relaxation of Continuous Disordered Systems." Phys. Rev. Lett., 77(21), pp. 4358-4361, 1996.
Barkema & Mousseau, "The Activation-Relaxation Technique: An Efficient Algorithm for Sampling Energy Landscapes." Comp. Mat. Sc., 20, p. 285-292, 2001.
Ben-Nun, M., & Martinez, T., "Photodynamics of Ethylene: Ab Initio Studies of Conical Intersections." Chemical Physics, 259, pp. 237-248, (2000).
Ben-Nun, M., & Martinez, T., "Ab Initio Quantum Molecular Dynamics." Advances in Chemical Physics, 121, pp. 439-512 (2002).
Ben-Nun, M., Quenneville, J., & Martinez, T., "Ab Initio Multiple Spawning: Photochemistry from First Principles Quantum Molecular Dynamics." Journal of Physical Chemistry, A, 104(22), pp. 5161-5175, (2000).
Boisvert & Lewis, "Self-diffusion of Adatoms, Dimers, and Vacancies on Cu(100)." Phys. Rev. B, 56(12), pp. 7643-7655, 1997.

Bouar & Soisson, "Kinetic Pathways from Embedded-Atom-Method Potentials: Influence of the Activation Barriers." Phys. Rev. B, 65(9), 094103, 2002.
Cai, Kalos, De Koning, & Bulatov, "Importance Sampling of Rare Transition Events in Markov Processes." Phys. Rev. E, 66(4), 046703, 2002.
Cleri, F., Rosato, V., "Tight-binding potentials for transition metals and alloys." Phys. Rev. B, 48, p. 22, 1993.
Deb, K., & Agarwal, R., "Simulated Binary Crossover for Continuous Search Space." Complex Systems, 9, pp. 115-148, (1995).
Deb, K., Pratap, A., Agarwal, S., & Meyarivan, T., "A Fast Elitist Non-dominated Sorting Genetic Algorithm for Multi-objective Optimization: NSGA-II." IEEE Transactions on Evolutionary Computation, 6(2), pp. 182-197, (2002).
U.S. Appl. No. 11/343,195, filed Jan. 30, 2006, David E. Goldberg.
Deshpande, "Relationship Between Fracture Toughness, Fracture Path, and Microstructure of 7050 Aluminum Alloy: Part I. Quantitative Characterization." Metal Transactions A, 29A, pp. 1191-1201, 1998.
Dewar, M., & Thiel, W., "The MNDO Method: Approximations and Parameters." Journal of the American Chemical Society, 99(15), pp. 4899-4907, (1977).
Dewar, M., Zoebisch, E., Healy, E., & Stewart, J., "AM1: A New General Purpose Quantum Mechanical Molecular Model." Journal of the American Chemical Society, 107(13), pp. 3902-3909, (1985).
Diaz De La Rubia, et al., "Self-decay-induced Damage Production and Micro-structure Evolution in FCC Metals: An Atomic-Scale Computer Simulation Approach." J. Comp.-Aided Mat. Design, 5, pp. 243-264, 1998.
Fichthorn & Weinberg, "Theoretical Foundations of Dynamical Monte Carlo Simulations." J. Chem. Phys., 95(2), pp. 1090-1096, 1991.
Fish & Schwab, "Towards Constitutive Models Based on Atomistics." International Journal for Multiscale Computational Engineering, 1(1), pp. 43-56, 2003.
Girifalco & Weizer, "Application of the Morse Potential Function to Cubic Metals." Phys. Rev., 114(3), pp. 687-690, 1959.
Goldberg, D., Deb, K., & Clark, J., "Genetic Algorithms, Noise and the Sizing of Populations." Complex Systems, 6, pp. 333-362, (1992).
Grujicic, Cao & Joseph, "Multiscale Modeling of Deformation and Fracture of Polycrystalline Lamellar $\gamma$-TiAl + $\alpha_2$-Ti$_3$ Al Alloys." International Journal for Multiscale Computational Engineering, 1(1), pp. 1-21, 2003.
Hamilton, Dawe, & Foiles, "Dislocation Mechanism for Island Diffusion on fcc (111) Surfaces." Phys. Rev. Lett., 74(14), pp. 2760-2763, 1995.

(Continued)

*Primary Examiner* — Mary Zeman
(74) *Attorney, Agent, or Firm* — Greer Burns & Crain Ltd

(57) ABSTRACT

Embodiments of the present invention provide, among other things, methods, apparatus, and systems for tuning a semiempirical process for predicting energy for different molecular configurations. In an example method, an energy value and an energy gradient are determined for each of a plurality of molecular configurations using an accurate method. A functional form of the semiempirical process is optimized using the determined energy values and energy gradients via multiobjective optimization. The functional form relates one or more parameters to energy values and energy gradients.

21 Claims, 21 Drawing Sheets

OTHER PUBLICATIONS

Harik, G., Cantu-Paz, E., Goldberg, D., & Miller, B., "The Gambler's Ruin Problem, Genetic Algorithms, and the Sizing of Populations." Evolutionary Computation, 7(3), pp. 231-253, (1999).

Haynes, et al., Type Inheritance in Strongly Typed Genetic Programming. In Angeline & Kinnear, Advances in Genetic Programming 2, (Chapter 18, pp. 359-376). Cambridge, MA: MIT Press (1996).

Henkelman & Jonsson, "A Dimer Method for Finding Saddle Points on High Dimensional Potential Surfaces Using Only First Derivatives." J. Chem. Phys., 111(15), pp. 7010-7022, (1999), ibid 113, 9978 (2000), ibid 115, 9657 (2001).

Jacobsen, Cooper & Sethna, "Simulations of Energetic Beam Deposition: From Picoseconds to Seconds." Phys. Rev. B, 58(23), pp. 15847-15865, 1998.

Kassner & Perez-Prado, "Five-power-law Creep in Single Phase Metals and Alloys." Progress in Materials Science, 45, 1-102, 2000.

King, H., "Quantitative Size-Factors for Metallic Solid Solutions." J. Mater. Sci., 1, p. 79, 1966.

Kinnear, "Alternatives in Automatic Function Definition: A Comparison of Performance." In Kinnear, K.E. (Ed.), Advances in Genetic Programming. (Chapter 6, pp. 119-141), Cambridge, MA: MIT Press (1996a).

Koza, "Hierarchical Genetic Algorithms Operation on Populations of Computer Programs." Proceedings of the 11th International Joint Conference on Artificial Intelligence, 1, pp. 768-774, 1989.

Levanov, et al., "Energetics of Co adatoms on the Cu(001) surface." Phys. Rev. B, 61, 2230, 2000.

Mazzone, et al., "Molecular-dynamics calculations of thermodynamic properties of metastable alloys." Phys. Rev. B, 55, p. 837, 1997.

Montana, "Strongly Typed Genetic Algorithm." Evolutionary Computation, 3(2), pp. 199-230, 1995. (Also BBN Technical Report No. 7866).

Mukherjee, Fedder, Ramaswamy & White, "Engineering Simulation Approaches for Micromachined Devices." IEEE Transactions on Computer-Aided Design of Integrated Circuits and Devices, 19(12), pp. 1572-1589, 2000.

Pelikan & Goldberg, "Escaping Hierarchical Traps with Competent Genetic Algorithms." Proceedings of the Genetic and Evolutionary Computation Conference, pp. 5111-518, 2001. (Also IlliGAL Report No. 2000020).

Quenneville, J., Ben-Nun, M., Martinez, T., "Photochemistry from first principles—advances and future prospects." J. Photochem. Photobiol., 144, p. 229, 2001.

Radloff, W., Stert, V., Freudenberg, T., Hertel, I., Jouvet, C., Dedonder-Lardeux, C., & Solgadi, D., "Internal Conversion in Highly Excited Benzene and Benzene Dimer: Femtosecond Time-resolved Photoelectron Spectroscopy." Chemical Physics Letters, 21(1-3), pp. 20-26, (1997).

Ratle & Sebag, "Grammar-guided Genetic Programming and Dimensional Consistency: Application to Non-parametric Identification in Mechanics." Applied Soft Computing, 1, pp. 105-118, 2001.

Ryan, Collins & O'Neill, "Grammatical Evolution: Evolving Computer Programs for an Arbitrary Language." Proceedings of the EuroGP Conference, 1391, pp. 83-96, 1998. (LNCS).

Sastry, K., Johnson, D., Thompson, A., Goldberg, D., Martinez, T., Leiding, J., Owens, J., "Multiobjective Genetic Algorithms for Multiscaling Excited State Direct Dynamics in Photochemistry." Proc. of the 8th annual conference on Genetic and evolutionary computation, pp. 1745-1752 (2006).

Sastry, K., Johnson, D., Goldberg, D., & Bellon, P., "Genetic Programming for Multi-timescale Modeling." Physical Review B, 72, 085438 (2005).

Sastry & Goldberg, "Probabilistic Model Building and Competent Genetic Programming." In Riolo, R., et al. (Eds.), Genetic Programming, Theory and Practice. Chapter 13, pp. 205-220. Boston, MA: Kluwer Academic Publishers (2003). (Also IlliGAL Report No. 2003013).

Sastry, O'Reilly, Goldberg, "Building-block Supply in Genetic Programming." In Riolo, R., et al., (Eds.), Genetic Programming Theory and Practice. Chapter 9, pp. 155-172. Boston, MA: Kluwer Academic Publishers (2003). (Also IlliGAL Report No. 2003012).

Sastry, K. & Goldberg, D., "Modeling Tournament Selection with Replacement Using Apparent Added Noise." Intelligent Engineering Systems Through Artificial Neural Networks, 11, pp. 129-134 (2001).

Sastry, K., Johnson, D., Goldberg, D., & Bellon, P., "Genetic Programming for Multiscale Modeling." Int. J. of MultiScale Comput. Eng., 2(2), pp. 239-256 (2004).

Sorensen & Voter, "Temperature-accelerated Dynamics for Simulation of Infrequent Events." J. Chem. Phys. 112(21), pp. 9599-9606, 2000.

Steiner & Genilloud, "Simple Bias Potential for Boosting Molecular Dynamics with the Hyperdynamics Scheme." Phys. Rev. B, 57(17), pp. 10236-10239, 1998.

Van Der Ven & Ceder, "First Principles Theory of Ionic Diffusion with Nondilute Carriers." Phys. Rev. B, 64(18), p. 184307, 2001.

Voter, "Hyperdynamics: Accelerated Molecular Dynamics of Infrequent Events." Phys. Rev. Lett., 78(20), pp. 3908-3911, 1997.

Voter, "Parallel Replica Method for Dynamics of Infrequent Events." Phys. Rev. B, 57(22), pp. R13985-R13988, 1998.

Voter, Montalenti & Germann, "Extending the Time Scale in Atomistic Simulation of Materials." Annu. Rev. Mater. Res., 32, pp. 321-346, 2002.

Pelikan, "Bayesian Optimization Algorithm: From Single Level to Hierarchy." Doctoral Dissertation, University of Illinois at Urbana-Champaign, Urbana, IL, 2002. (Also IlliGAL Report No. 2002023).

Stepanyuk, et al., "Strain relief and island shape evolution in heteroepitaxial metal growth," Phys. Rev. B, 62, 15398, 2000.

Stepanyuk, et al., "Strain and adatom motion on mesoscopic islands," Phys. Rev. B, 63, 153406, 2001.

Stepanyuk, et al., "Burrowing of Co clusters on the Cu(001) surface: Atomic-scale calculations," Phys. Rev. B, 63, 235406, 2001.

Stewart, J. "Optimization of Parameters for Semiempirical Methods 1. Method." Journal of Computational Chemistry, 10(2), pp. 209-220 (1989).

Toniolo, A., Thopmson, A., Martinez, T., "Excited State Direct Dynamics of Benzene with Reparameterized Multireference Semiempirical Configuration Interaction Methods." Chemical Physics, 304, pp. 133-145 (2004).

\* cited by examiner

FIG. 12A
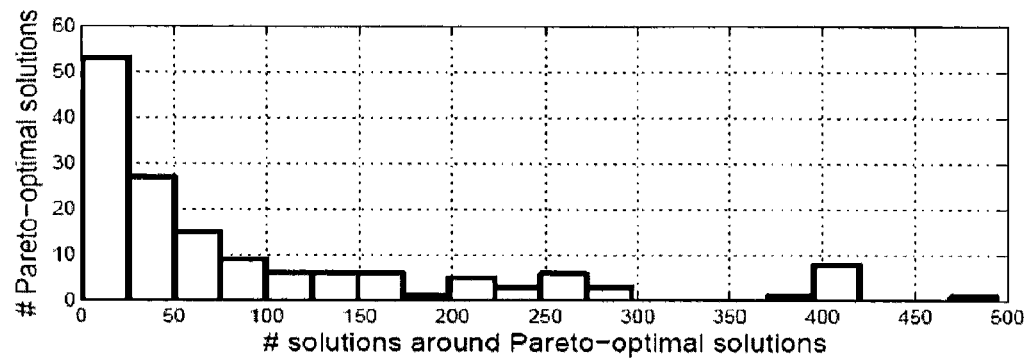
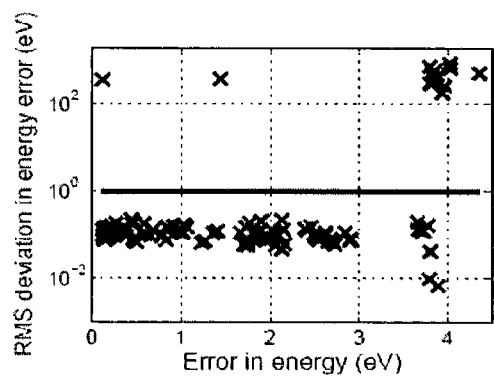
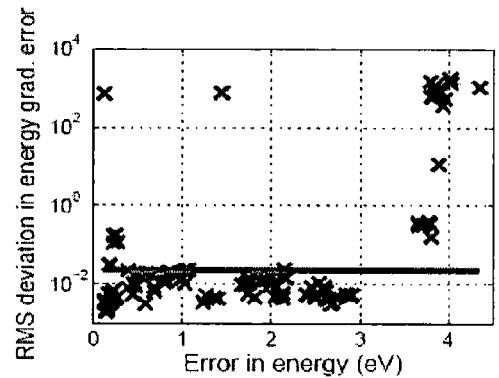
FIG. 12B FIG. 12C

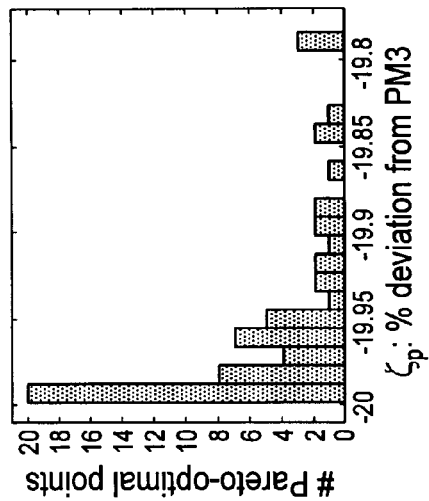
FIG. 19E
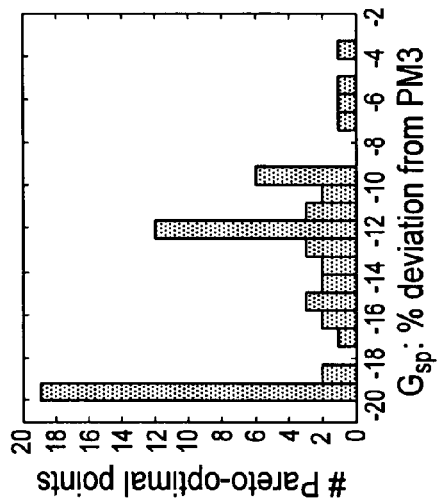
FIG. 19F
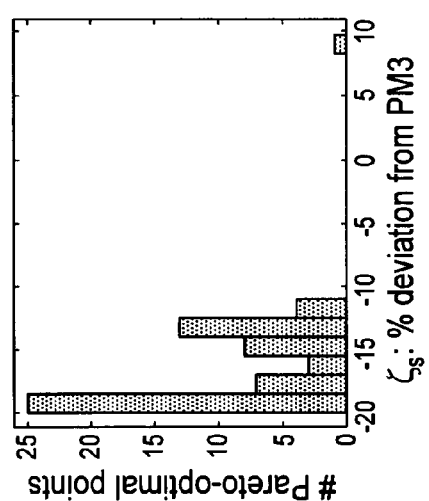
FIG. 19G
FIG. 19H

QUANTUM CHEMISTRY SIMULATIONS USING OPTIMIZATION METHODS

PRIORITY CLAIM AND REFERENCE TO RELATED APPLICATION

This application claims the benefit of U.S. Provisional Application Ser. No. 60/898,952, filed Jan. 31, 2007, under 35 U.S.C. §119.

STATEMENT OF GOVERNMENT INTEREST

The present invention was made with Government assistance under Air Force Office of Scientific Research (AFOSR) Grant No. FA9550-06-1-0096 and National Science Foundation (NSF) Grant No. DMR-03-25939. The Government has certain rights in this invention.

FIELD OF THE INVENTION

The invention relates generally to the fields of simulations, analysis, and predictions for chemical, biological, biochemical, pharmaceutical, and/or physical phenomena. The invention further relates generally to the field of optimization methods.

BACKGROUND OF THE INVENTION

Photochemical reactions are fundamental in many biological (e.g., photosynthesis and vision) and technological (e.g., solar cells and light emitting diode (LED) displays) settings. Such reactions, as well as many spectroscopic measurements, involve electronic excited states of molecules and their concomitant structural changes. The reactions and associated dynamics are energetically subtle and require highly accurate descriptions of the relevant molecular forces. It is highly desirable in the art to be able to simulate and predict results for these and other types of reactions. One exemplary benefit of simulating and predicting reactions is to limit the amount of real-world experimental reactions needed. For example, this may avoid useless chemical combinations and may provide new combinations not previously considered. However, conventional simulation and prediction methods have been inadequate for several reasons.

Reliable methods for prediction are computationally very expensive even for small molecular reactions, and rapidly approach the impossible for reactions in complex environments, such as in solvents (e.g., water), in solid cages (e.g., zeolites), or with more complex molecules, such as proteins (e.g., protein ion channels). Hence, having very fast semiempirical potentials that accurately reproduce higher-level quantum chemistry results would make it possible to address critical biological processes and technologically useful chemical reactions, or dramatically reduce searches for potentially technologically useful light-activated reactions.

Established semiempirical quantum chemistry methods, known by acronyms such as MNDO, AM1, and PM3 with well-established parameter databases, and software, such as MOPAC, MOLCAS, and MOLPRO, have had parameter sets hand-designed and optimized to predict ground-state energies—not excited state energies. For ethylene, for example, AM1 or PM3 parameter sets incorrectly obtain a pyramidalized structure as the lowest-energy excited state. Thus, the carefully established parameter sets yield inaccurate potential energy surfaces and unphysical reaction dynamics. Further, previous reoptimization attempts to improve excited-state potential energy surfaces have met with limited success.

SUMMARY OF THE INVENTION

Embodiments of the present invention provide, among other things, methods, apparatus, and systems for tuning a semiempirical process for predicting energy for different molecular configurations. In an example method, an energy value and an energy gradient are determined for each of a plurality of molecular configurations using an accurate method. A functional form of the semiempirical process is optimized using the determined energy values and energy gradients via multiobjective optimization. The functional form relates one or more parameters to energy values and energy gradients.

BRIEF DESCRIPTION OF THE DRAWINGS

FIG. 12A shows a histogram of a density of parameter sets around (within 2% of) Pareto-optimal solutions; FIG. 12B shows RMS deviation in error in energy between the Pareto-optimal solutions and corresponding neighboring parameter sets; and FIG. 12C shows RMS deviation in error in energy gradient between the Pareto-optimal solutions and corresponding neighboring parameter solutions;

FIGS. 19A-19K are histograms of the deviation of eleven stable, accurate, and optimal semiempirical parameters for ethylene, including $U_{ss}$(FIG. 19A), $U_{pp}$(FIG. 19B), $\beta_p$(FIG. 19D), $\varsigma_s$(FIG. 19E), $\varsigma_p$(FIG. 19F), $G_{ss}$(FIG. 19G), $G_{sp}$(FIG. 19H), $G_{pp}$(FIG. 19I), $G_{p2}$(FIG. 19J), and $H_{sp}$(FIG. 19K) from their corresponding PM3 parameter values.

DETAILED DESCRIPTION

Figure 1:
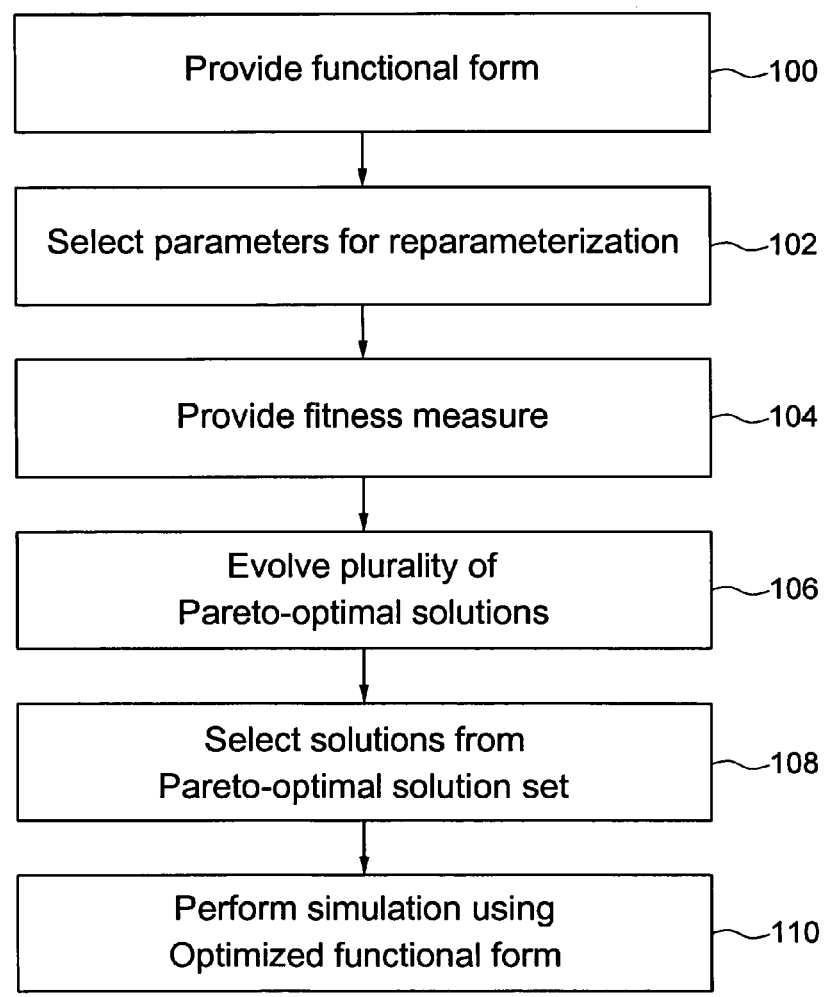
FIG. 1 shows a method for evolving a functional form, according to an embodiment of the present invention.

A comprehensive understanding of the photochemistry of molecules requires bridging the gap between molecular dynamics and quantum chemistry. Quantum dynamic simulations require simultaneous solution of both nuclear and electronic Schrodinger equations. Additionally, the potential energy surfaces (PES) must be of high quality and very robust, because the portions of the PES that are critical to the behavior of a molecule may be far removed from the Franck-Condon region (the directly excited-state portion of the PES).

The ab initio multiple spawning (AIMS) method has been developed to address such problems. While the AIMS method is extremely flexible and accurate (for example, it can describe quantum mechanical phenomena such as tunneling and non-adiabatic transitions), it is computationally very expensive, especially for large molecules, due to the large number of ab initio electronic structure calculations involved, making long-time dynamics simulations highly improbable, if not impossible.

Thus, having substantially faster, semiempirical methods that accurate reproduce higher-level quantum chemistry results would make it possible to address critical biological processes and technologically useful chemical reactions. To retain the flexibility of ab initio methods with less computational cost, semiempirical methods that ignore some integrals of ab initio methods and use fit parameters for others were developed. Instead of calculating each electron integral, semiempirical methods make certain approximations. For example, many two electron integrals (those on three or four centers) are neglected (assumed to be zero). Further, the remaining one and two electron integrals are replaced with analytic functions that depend on a set of parameters. Semiempirical methods are significantly less expensive than AIMS, but have an accuracy that depends of the accuracy of the semiempirical parameters. The semiempirical parameters, which are different for each element, have traditionally been hand-designed and optimized for a small set of molecules without the use of fractional occupation molecular orbitals. Such parameters predict ground state properties for a set of molecules, but not excited-state energies.

For example, standard parameter sets in quantum chemistry databases, known by acronyms such as MNDO, AM1, and PM3, and software yield useful information concerning ground-state energies (the locations of the minimal energy conical intersections (MECIs)), which often dominate photochemical reactions. However, they often fail to yield globally accurate potential energy surfaces critical for accurate photochemical reaction simulation. AM1 parameter sets in ethylene, for example, incorrectly obtain the so-called pyramidalized structure as the excited-state minimum. These carefully established parameter sets often yield inaccurate potential energy surfaces, resulting in unphysical excited-state reaction dynamics.

Therefore, to obtain globally accurate energetics, the parameter sets must be reoptimized for different classes of molecules using a very limited set of ab initio and/or experimental data. This so-called reparametrization strategy is a promising way to extend direct dynamics simulations of photochemistry to more realistic multi-picosecond time scales. It is also reasonable to expect transferability of the parameter sets optimized on simple molecules, such as ethylene and benzene, to other, complex molecules, such as stilbene and phenylacetylene dendrimers. Furthermore, the reparametrization approach opens up the possibility of accurate simulations of photochemistry in complex environments such as proteins and condensed phases.

The reoptimization problem is massively multimodal and involves multiple conflicting and competing objectives, such as minimizing the difference between calculated and predicted energies, gradients of energies, and stationary-point geometries. Conventional reparameterization methods, mostly based on a staged fixed-weight single-objective optimization, have only been partially successful, as the weights of different objectives often are unknown, and local search can get stuck in low-quality optima. Particularly, such methods have not yielded globally correct PES, and have produced unphysical dynamics.

Evolutionary algorithms, on the other hand, are robust search methods that simultaneously optimize multiple objectives, and thus are particularly suited for rapid reparameterization of semiempirical parameters. Thus, embodiments of the invention provide, among other things, the use of multi-objective optimization methods such as multiobjective evolutionary algorithms, including multiobjective genetic algorithms (MOGA), for rapid reparameterization of semiempirical methods to obtain globally-correct excited state dynamics. Moreover, unlike single-objective optimization methods, multiobjective evolutionary algorithms can process a number of solutions in parallel and find all or a majority of the diverse Pareto-optimal solutions, avoiding potentially irrelevant and unphysical pathways. This approach bridges high-level quantum chemistry and semiempirical methods, providing an accurate representation of complex molecular excited-state and ground-state behavior.

While the reparameterization procedure only fits energetics of a few important stationary molecular geometries, much larger portions of the PESs will be accessed during dynamics simulations. Therefore, preferred semiempirical methods should incorporate enough of the fundamental chemical physics to generate at least qualitatively correct global PESs. While it is possible to include geometries and energetics of the MECIs in the reparameterization, the strategy of using relatively little ab initio data (as a nonlimiting example, less than 0.1% of the possible configurations) is crucial if reparameterization is to be applicable for larger molecules, where ab initio data is extremely expensive to obtain. Therefore, example methods of the present invention deliberately use a minimal set of energies and gradients at ground state optimized geometries in reparameterization.

MOGAs can be used to reoptimize the parameter sets using a very limited set of known accurate data (e.g., ab initio and experimental data) to yield globally accurate potential energy surfaces and excited-states, providing accurate photochemical reaction dynamics. Use of MOGA, for example, can provide accuracy well beyond convention methods, or expectation of human experts. Additionally, a dramatic reduction (e.g., from ~100 to 1000 times) in computation cost can be achieved. This allows, for example, simulations for more complex molecules, which may be impractical or even impossible for methods such as AIMS.

In exemplary embodiments of the present invention, a method for tuning a semiempirical process for predicting energy for different molecular configurations includes determining an energy value for each of a plurality of molecular configurations using an accurate method, such as AIMS or use of experimental results. As a nonlimiting example, a number of "snapshots" may be taken for different configurations using AIMS. In some exemplary embodiments, this provides very accurate snapshots, but only for very few points. One or more functional forms of a semiempirical process are optimized using the determined energy values. Such functional forms preferably relate one or more parameters to energy values. Preferably, optimizing the functional forms includes optimizing the one or more parameters based on the determined energy values.

In preferred methods, at least one energy gradient is also determined for each of a plurality of molecular configurations using the accurate method. In this case, optimization further includes optimizing the one or more parameters based on the determined at least one energy gradient. In this way both the energy and the energy gradient can be addressed by optimizing the parameters using multiobjective optimization methods. In exemplary embodiments, one or more parameters are optimized to minimize differences (error) between calculated and predicted energies, and gradients of energies. Such multiobjective optimization may include, for example, multiobjective genetic algorithms (MOGA), which can provide Pareto-optimal solutions. Thus, one can optimize with different weights, providing a plurality of sets of parameters (that is, multiple solutions). Other objectives, such as geometries (e.g., stationary-point geometries), may be considered as well in multiobjective optimization methods. Simulations may be run using the optimized functional forms.

An example process for optimizing a functional form for a semiempirical process given data provided by an accurate method is shown in FIG. 1. Generally, a functional form is provided 100, either by selecting a previously provided function, or by evolving a function, for example, by genetic programming (GP). Evolving a functional form may occur with or without prior problem knowledge. An example method for evolving a functional form using GP uses techniques similar to that described in Sastry, Johnson, Goldberg, and Bellon, "Genetic Programming for Multiscale Modeling", International Journal for Multiscale Computational Engineering, 2(2)239-256 (2004); and Sastry, Johnson, Goldberg, and Bellon, "Genetic Programming for Multitimescale Modeling", Physical Review B 72, 085438 (2005). These two publications are incorporated herein by reference in their entirety.

Given a functional form, parameters used in the functional form are selected 102 for reparameterization. Each of these parameters forms a decision variable for a search problem, so that a solution is made up of a string of the decision variables. More particularly, the decision variables are encoded into finite-length strings of alphabets of certain cardinality. Such strings are also referred to as chromosomes, the alphabets are referred to as genes, and the values of genes are referred to as alleles. In an exemplary embodiment, real-valued encoding is used, though other types of coding (binary, gray, permutation, program, etc.) are also contemplated. Problem knowledge may be used as needed or desired to select parameters.

Next, to evolve good solutions and implement natural selection, a fitness measure is provided 104, which considers predicted energies and energy gradients compared to energies and energy gradients determined using the accurate method. Fitness may be objective, subjective, or co-evolutionary, but it is preferred that the fitness evaluation be objective. Generally, it is also preferred that the parameter sets be optimized for a particular system and that the sets are fit to only a few important geometries for the molecule. The overall goal is to maintain an accurate description of ground-state properties, and yield a globally accurate PES, including excited states.

In an example multiobjective genetic algorithm, multiple fitness functions are used: a first function minimizing the error between the predicted energy for a particular configuration and the energy determined using the accurate method; and a second function minimizing the error between the predicted energy gradient for a particular configuration and the energy gradient determined using the accurate method. The number of configurations preferably are a very limited set of excited-state and ground-state configurations determined using the accurate method. Also, the fitness functions (e.g., the energy error fitness function) can consider the difference between the predicted geometry and the geometry determined using the accurate method.

Unlike some conventional methods, these multiple fitness functions are not combined to provide a single objective, such as by providing a priori weights to each of the fitness functions and combining them. This is because the correct weights are usually not known a priori, and it is easy for a local search to get stuck in low-quality optima. Instead, embodiments of the present invention employ a multiobjective optimization given the multiple fitness functions.

Figure 2:
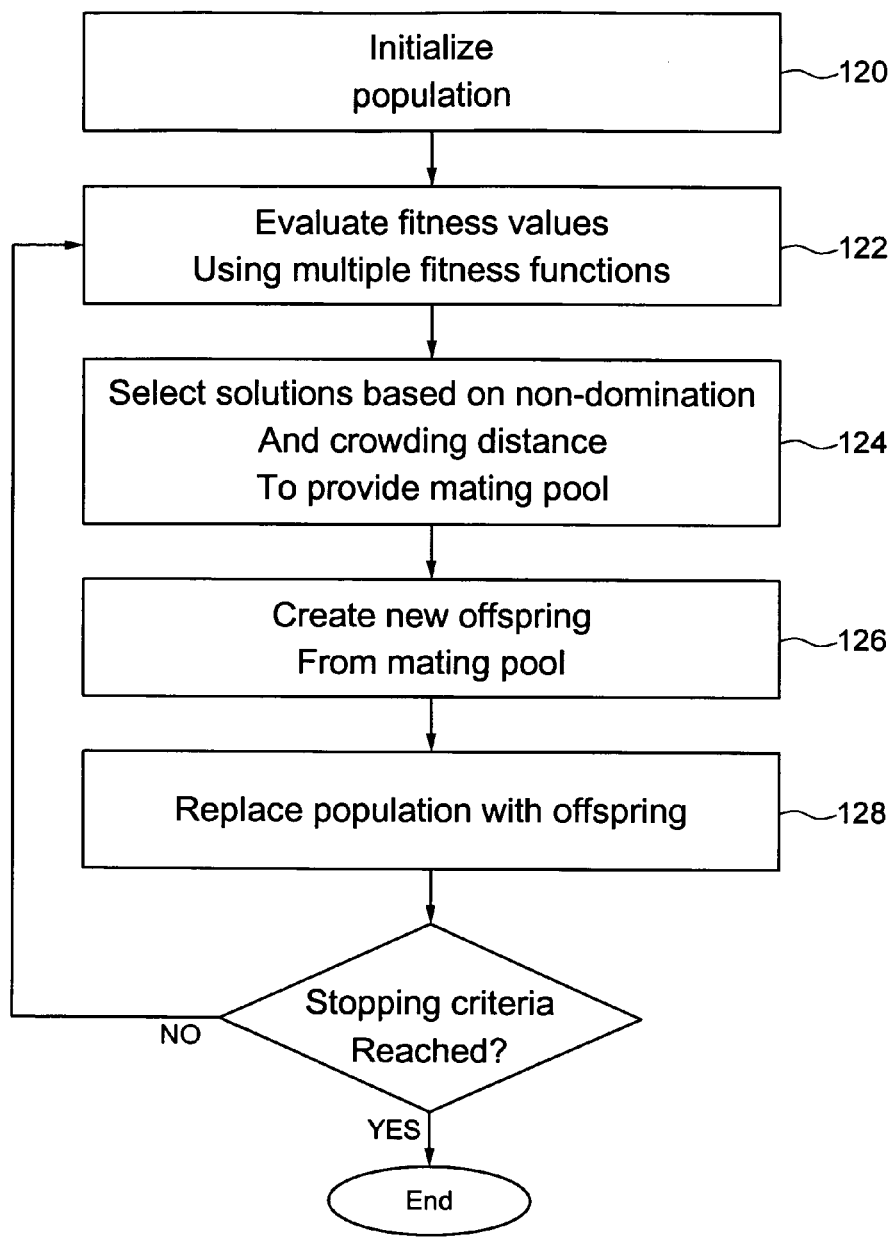
FIG. 2 shows a method for optimizing parameters for a semiempirical process, according to an embodiment of the present invention.

Given the functional form, the selection of parameters, and the multiple fitness functions, the example method then evolves 106 a plurality of solutions to the search problem. An example process for evolving solutions is shown in FIG. 2. First, the population is initialized 120 by selecting a population size and generating an initial population. Selecting a population size may be done, as a nonlimiting example, using population-sizing models, which are known to those of ordinary skill in the art. The population may be initialized randomly and/or according to particular criteria, such as criteria based on knowledge of the problem, closeness to existing parameters (e.g., existing parameter sets), etc.

Once the population is initialized (or an offspring population is created in later steps), the fitness values of the candidate solutions are evaluated 122. This may be done, for example, using the multiple fitness functions provided.

Selection takes place 124 for the example multiobjective genetic algorithm preferably based on "survival of the non-dominated". Particularly, preferred embodiments use non-dominated sorting to assign domination ranks to individuals in the population based on their multiple objective values. A candidate solution x may dominate y, for example, if x is no worse than y in all objectives and if x is better than y in at least one objective. By assigning all non-dominated solutions a low rank, assigning non-dominated solutions among the remaining solutions a next-highest rank, and so on, subsets of the population with different ranks are provided. This criteria is used to converge onto the Pareto-optimal solutions (the best non-dominated set of solutions).

Another, and preferably secondary, selection criteria that may be used is diversity or crowding distance; i.e., how dense the non-dominated (Pareto) front is in the neighborhood of the solution. Considering this criteria allows one to achieve good coverage or spread of solutions in the Pareto front, to maintain as diverse a distribution as possible.

Given the domination ranking and the crowding distance, the solutions can be selected for a mating pool for evolving new solutions. An exemplary selection process is s-wise tournament selection, without replacement. However, it will be appreciated that other selection processes are possible. The selection between solutions in the tournament may be based on a combination of the domination ranking and the crowding distance, preferably with the domination ranking having priority in selection. For example, the domination ranking may be used to first consider among solutions in a tournament, with the crowding distance used to select among solutions having the same domination rank. The selection preferably takes place until the mating pool has the same number of solutions (chromosomes) as the initial population.

The mating pool is then used to create new offspring 126. This may be done by recombination and/or mutation, as is known to those of ordinary skill in the art. Recombination combines parental traits to create offspring, while mutation slightly modifies an offspring. The result will be a new, and possibly better, solution that is not identical to any particular parent. Various methods for recombination and mutation are known to those of ordinary skill in the art, and the invention is not to be limited to particular methods of recombination and/or mutation. It will also be appreciated that particular methods of recombination and/or mutation lend themselves well to efficiency enhancements.

The offspring population created by selection, recombination, and mutation replaces the original parental population 128. Elitism, in which the best solutions from the parent and offspring population are retained for the next generation and are used to evolve new candidate solutions, may be used. The evolutionary process is then repeated until one or more stopping criteria are met 130.

Once stopping criteria are met, the example optimization method provides a plurality of Pareto-optimal solutions. Additional criteria may be used to select solutions 108 from among the evolved Pareto-optimal solutions. Such criteria may include, but is not limited to: 1) sensitivity to small perturbations; 2) ability to yield accurate excited- and ground-state energies for untested and critical configurations; and/or 3) ability to yield accurate excited-state dynamics.

For example, robustness of a particular parameter set may be analyzed. Small changes in the parameters (e.g., 0.1% or less) should have small effects on the error in energy and the error in gradient. In an example manual evaluation method, a small number (e.g., 10) parameter sets around each optimized parameter set may be selected, and error in energy and energy gradient may be calculated for each set. Points (sets) having large RMSE values (as a nonlimiting example, above 0.05 eV for error in energy and above 0.008 eV/Ang for error in energy gradient) can be removed as being too sensitive.

The GA population also contains data that can be mined, e.g., for sensitivity or parameter sets. Analysis of quality of solutions around the Pareto-optimal sets yields a good measure of the SE parameter stability. More perturb points in the MOGA analysis indicates higher reliability.

An example method for checking the ability to yield accurate excited-state dynamics includes determining a population transfer using a limited number (e.g., 20) of initial conditions for each parameter set. Parameter sets with lower error in energy gradient values have lifetimes close to ab initio value.

Given the selected solutions, simulations can be carried out 110. Particularly, using the optimized semiempirical methods, one or more molecular configurations (e.g., coordinates) may be input to the resulting functions to determine an energy and energy gradient.

Example Reparameterization—Ethylene and Benzene

A nonlimiting example method described herein reparameterizes two simple molecules, which are fundamental building blocks of organic molecules: ethylene and benzene. The photochemistry of ethylene has been studied as a prototype for cis-trans isomerization. The small size of ethylene has many advantages. First, semiempirical calculations can be run very quickly, so a large number of reparameterization runs can be conducted. Second, the small number of atoms, basis functions, and possible geometries imply that the results may be less complex and more easily interpretable. Lastly, the size and simplicity enables the reoptimized parameter sets to be amenable for further analysis of ethylene dynamics and for transferability to stilbene or conjugated polyenes. However, despite its simplicity, ethylene has an associated set of ethylidene geometries that can be used to evaluate performance of the reoptimized parameter sets in calculations for which they were not optimized. Benzene plays an important role in photochemistry and photophysics of aromatic system and has been extensively studied both experimentally and theoretically.

For ethylene reparameterization, the example method uses energetics for the ground state planar and ethylidene geometries, twisted geometry on the excited state as well as the gradients on the excited and ground states. The ab initio results used for reparameterization are taken from previously reported calculations (Ben-Nun & Martinez, Photodynamics of ethylene: Ab initio studies of conical intersections, Chemical Physics, 259, 237-248) and are calculated using CASSCF (2/6)*SDCI wavefunctions with the aug-cc-pVDZ basis set. For reparameterization of benzene, we use four important local minima on $S_0$: planar, Dewar benzene, prefulvene, and benzvalene. We use ab initio calculations and experimental results reported in and used by Toniolo, Thompson, and Martinez, Excited state direct dynamics of benzene with reparameterized multireference semiempirical configuration interaction methods, Chemical Physics, 304, 133-145 (2004).

A floating occupation molecular orbital-configuration interaction (FOMO-CI) calculation is used to describe electronic excited states. The molecular orbitals are optimized using an SCF calculation in which the occupation numbers of some of the orbitals are allowed to fluctuate. These occupation numbers are updated at each SCF iteration according to $$O_i = \int_{-\infty}^{\varepsilon_F} \sqrt{\frac{2}{\pi \omega^2}} \, e^{-\frac{(\varepsilon-\varepsilon_i)^2}{2\omega^2}} \, d\varepsilon$$

where $O_i$ is the occupation number at orbital i, $\omega$ is the width of the Gaussian function, $\varepsilon_i$ is the energy of orbital i, and $\varepsilon_F$ is the Fermi level energy determined such that $$\sum_i O_i = N_{eelectrons}$$

where $N_{electrons}$ is the number of electrons in the system. While all orbitals could be allowed to have fractional occupation, only the occupation numbers of orbitals in the active space are allowed to vary. The benefit of this method is that it is a fast, low-cost way of generating better virtual orbitals, which improves the treatment of excited states.

To calculate the excited state properties, multiple configurations need to be included in the wavefunction. Using the floating occupation molecular orbitals, we use a complete active space configuration interaction (CAS*CI) wavefunction. In this technique, all the configurations that involve excitations within the active orbitals defined in the calculation are included. The energies of each of the configurations are calculated using the fractionally occupied orbitals, but the orbitals are not reoptimized at each step.

The semiempirical calculations are performed with a developmental version of MOPAC2000, while the ab initio results are performed with MOLPRO and MolCas. For both ethylene and benzene, 11 semiempirical parameters for carbon—$U_{ss}$, $U_{pp}$, $\beta_s$, $\beta_p$, $\zeta_s$, $\zeta_p$, $G_{ss}$, $G_{sp}$, $G_{pp}$, $G_{p2}$ and $H_{sp}$—are reoptimized. A real-valued encoding is used to represent the parameters. Following some earlier methods, the core-core repulsion parameters—$\alpha$, $a_i$, $b_i$, and $c_i$—are not reoptimized.

The reparameterization of the semiempirical methods involve multiple objectives and yield a set of optimal solutions, also known as Pareto-optimal solutions, instead of a single optimal solution. Since no one Pareto-optimal solution is better than the other—without additional information or decision-making choice—the goal of multi-objective optimization is to search for all Pareto-optimal solutions. Traditional approaches for handling multi-objective problems usually convert multiple objectives into single-objective problems by using a priori weights denoting the relative importance of the different objectives. Such approaches rely on multiple runs of single-objective optimization with different weights to obtain different Pareto-optimal solutions. However, the choice of weights is a non-trivial task, and uniform coverage of the Pareto-optimal front is usually improbable—sometimes, impossible—and the methods are usually inefficient and less robust.

On the other hand, population-based approaches using genetic and evolutionary algorithms can directly deal with multiple objectives and simultaneously maintain a diverse set of solutions. Therefore, genetic algorithms can be used to find multiple Pareto-optimal solutions in a single simulation run. The Pareto-optimal solutions can be exploited to select solutions appropriate for each particular application without having to weigh the objectives in advance or reduce the multiple objectives in some way.

As known by those of ordinary skill in the art, genetic algorithms (GAs) encode the decision variables into finite-length strings of alphabets of certain cardinality. The strings, which are candidate solutions, are referred to as chromosomes, the alphabets are referred to as genes, and the values of genes are called alleles. An exemplary method uses a real-valued encoding to represent the 11 parameters of the semiempirical methods. In this example, an upper and a lower bound are specified around the PM3 value for each semiempirical parameter and a real value between the specified bounds represents a possible semiempirical value. Therefore, a chromosome in this example consists of 11 real-valued genes corresponding to each of the 11 semiempirical parameters. However, it will be appreciated by those of ordinary skill in the art that other representations, such as binary, gray, permutation, real number, program functions, etc. are possible.

To evolve good solutions and to implement natural selection, GAs rely on a notion of fitness, or a relative goodness measure of a candidate solution. Generally, fitness can be objective, subjective, co-evolutionary, etc. The two fitness functions used in this example involve minimizing the absolute error in energies and energy-gradients, respectively, for a very limited set of excited-state and ground-state configurations either calculated by ab initio methods or obtained by experiments, and those predicted by semiempirical methods.

That is, $$f_1(x) = \sum_{i=1}^{n_c} [|\Delta E_{0,i} - \Delta E_{SE,i}(x)|]$$

$$f_2(x) = \sum_{i=1}^{n_g} |(\nabla E_{0,i}) - (\nabla E_{SE,i}(x))|$$

where x represents the semiempirical parameters to be optimized, $n_c$ is the number of configurations, and $n_g$ is the number of gradient-energy data used in reparameterization. $\Delta E_{0,i}$ and $\Delta E_{SE,i}$ are the differences in energy between the geometry i and the reference structure (planar ethylene and benzene) calculated by ab initio and semiempirical methods, respectively.

For ethylene, we make the restriction that the excited state at the ground state planar geometry must have the correct state symmetry. For benzene, in the first objective we also include geometry difference between the reparameterized semiempirical geometries and the ab initio geometries, $\Delta G_{0,SE,i}$, by calculating the sum-squared differences between the corresponding atoms after the molecules have been rotated and translated such that they are in maximum coincidence. $\nabla E_{0,i}$ and $\nabla E_{SE,i}$ represent the excited-state energy gradients using ab initio and semiempirical methods, respectively. The semiempirical calculations are done within a development version of MOPAC2000 using a CAS(2/2)*CI wavefunction. All geometries are minimized, and then energy gradients are calculated at this minimum on the potential energy surface.

Once the problem is encoded in a chromosomal manner and a fitness measure for discriminating good solutions from bad ones has been chosen, we can start to evolve solutions to the search problem. The initial population of candidate solutions is usually generated randomly across the search space. However, domain-specific knowledge or other information can be easily incorporated in the generation of the initial population. In this example reparameterization of semiempirical potentials, the initial population is randomly generated within a certain percentage (20-50%) of the PM3 parameter values. The parameter bounds are restricted around the PM3 set so as to maintain a reasonable representation of the ground-state potential energy surface.

The multiobjective GA used in this example is the non-dominated sorting genetic algorithm II (NSGA-II), with binary (s=2) tournament selection without replacement, simulated binary crossover (SBX)—which models the behavior of single-point crossover in binary genetic algorithms—with $\eta_c=5$ and crossover probability $p_c=0.9$, and a polynomial mutation with $\eta_n=10$ and mutation probability $p_m=0.1$. The population size n=800 is determined in accordance with population-sizing models, as would be understood by those of ordinary skill in the art.

Figure 3:
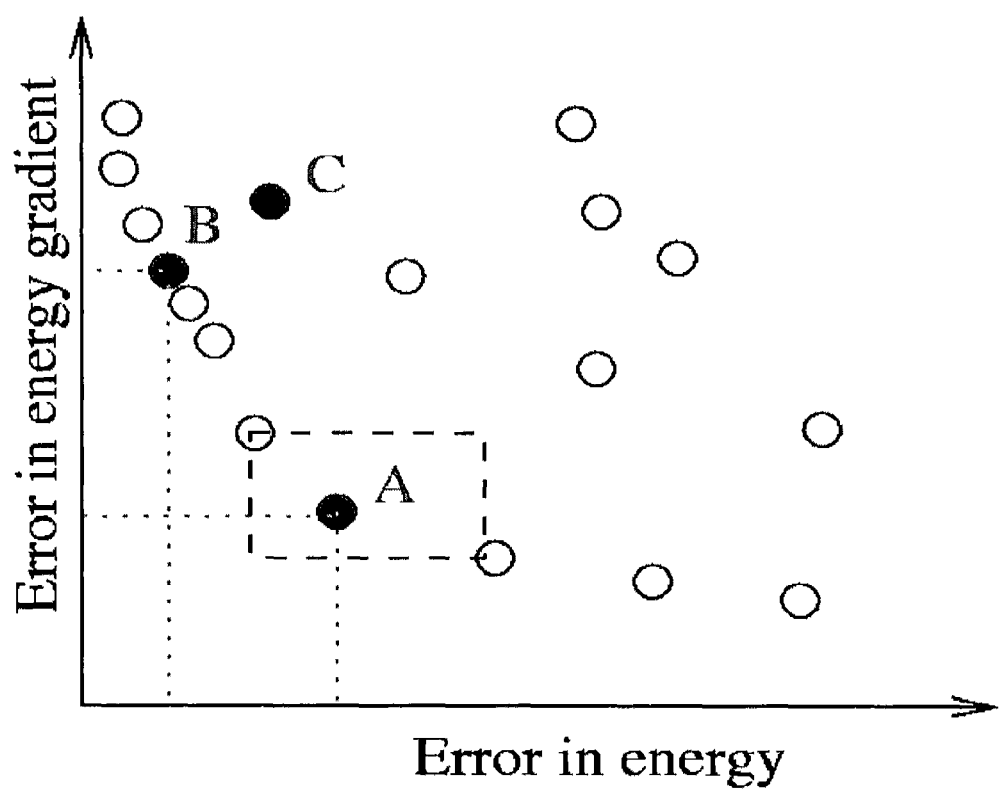
FIG. 3 illustrates non-domination and crowding for a two-objective minimization problem.

Once the population is initialized or an offspring population is created, the fitness values of the candidate solutions are evaluated. Non-dominated sorting assigns domination ranks to individuals in the population based on their multiple objective values. A candidate solution x dominates y, if x is no worse than y in all objectives and if x is better than y in at least one objective. For example, as shown in FIG. 3, solution B is preferred and dominates solution C, whereas solutions A and B are non-dominant.

Figure 4:
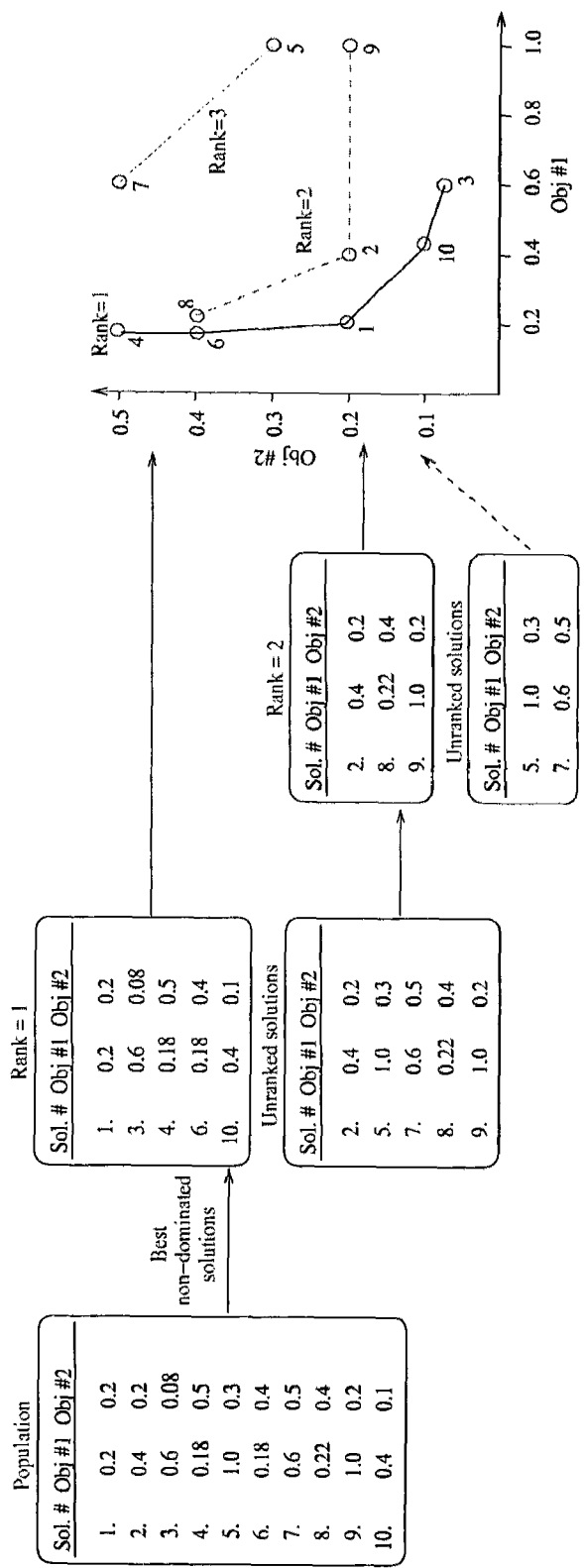
FIG. 4 shows an example non-dominated sorting procedure.

In an example non-dominated sorting method, we start with the set of solutions that are not dominated by any solution in the population and assign them rank 1. Next, solutions that are not dominated by any of the remaining solutions are assigned rank 2. That is, all solutions with rank 2 are dominated by at least one solution with rank 1, but are not dominated by others in the population. Thus, the sorting and ranking process continues by assigning increasing ranks to those solutions that are not dominated by any of the remaining unranked solutions. After non-dominated sorting, we are left with subsets of population with different ranks. An example of this sorting for a two objective minimization problem is shown in FIG. 4. Solutions with a given rank are not dominated by solutions that have the same rank or higher and are dominated by at least one solution with a lower rank. Therefore, with respect to Pareto optimality, solutions with lower ranks should be given priority.

Apart from finding solutions in the Pareto front, it is also preferred to achieve good coverage or spread of solutions in the front to maintain as diverse a distribution as possible. The diversity of solutions in the objective space is usually maintained with a niching mechanism, and NSGA-II uses crowding for doing so. In an example method, each solution in the population is assigned a crowding distance, which estimates how dense the non-dominated front is in the neighborhood of the solution. Therefore, the higher the crowding distance of the solution, the more diverse the solution is in the non-dominated front. For example, in FIG. 3, solution A is more crowded, and hence more diverse, than solution B. The pseudocode for computing the crowding distance is outlined below:

```
crowding_distance_computation(P)
    for rank r = 1 to R
        P_r = subset of solutions in P with rank r
        n_r = size(P_r)
        for i = 1 to n_r
            d_c(P_r(i)) = 0
            for j = 1 to M
                Q_r = sort P_r using j^th objective, f_j.
                d_c(Q_r(1)) = d_c(Q_r(n_r)) = ∞
                for i = 2 to n_r-1
                    dist = Q_r(i+1).f_j - Q_r(i-1).f_j
                    d_c(Q_r(i)) = d_c(Q_r(i)) + dist
                end
            end
        end
    end
    return d_c
``` where, P is the population, R is the maximum rank assigned in the population, M is the number of objectives, and $Q_r(i) \cdot f_j$ is the value of $j^{th}$ fitness value of the $i^{th}$ individual.

The selection process allocates more copies to solutions with better fitness values and thus imposes the survival-of-the-fittest mechanism on the candidate solutions. The main idea of selection is to prefer better solutions to worse ones. Again, an example selection process uses a binary (s=2) tournament selection without replacement. In tournament selection without replacement with tournament size s, s chromosomes are chosen at random without replacement and entered into a tournament against each other. The best (fittest) individual in the group of s chromosomes wins the tournament and is selected into a mating pool for evolving new solutions. The tournaments are continued until all the individuals in the population have competed once, at which point there are exactly n/2 chromosomes in the mating pool, where n is the population size (the population size being an exact multiple of the tournament size). The entire process is repeated again— but this time the competitors in each tournament will be different—so that the mating pool has n chromosomes.

As multiple objectives are dealt with, the best individual in a tournament is based on the notion of non-domination and niching. That is, NSGA-II uses an individual comparison operator to compare the quality of two solutions and to select the better one. Both the rank and the crowding distance of the two solutions are used in the comparison operator, a pseudo-code of which is given below. First, ranks of the two individuals are considered and the solution with a lower rank is selected. If the two individuals have the same rank, then the solution with the highest crowding distance is selected.

```
compare(x,y)
    if rank(x) < rank(y) then return x
    if rank(x) > rank(y) then return y
    if rank(x) = rank(y)
        if d_c(x) > d_c(y) then return x
        if d_c(x) < d_c(y) then return y
        if d_c(x) = d_c(y) then randomly choose either x or y
    End
```

Recombination combines bits and pieces of two or more parental solutions to create new, possibly better solutions (i.e., offspring). There are many ways to accomplish this, as will be appreciated by one of ordinary skill in the art. Achieving competent performance depends on getting the recombination mechanism designed properly, but is significant that the offspring under recombination should not be identical to any particular parent and will instead combine parental traits in a novel manner.

In SBX, individuals in the mating pool are divided into random pairs, and each pair undergoes recombination with a probability $p_c$. For each pair participating in the crossover, each gene (or variable) undergoes contracting or expanding crossover operation with a probability 0.5. Therefore, for each pair of chromosomes undergoing recombination on an average half of the genes are modified using either contracting or expanding crossover operations. Assuming that the two parents $p_1$ and $p_2$ recombine to yield offspring $c_1$ and $c_2$, let $x_i^{p_1}$ and $x_i^{p_2}$ be the $i^{th}$ gene-value of parents $p_1$ and $p_2$ respectively. Without loss of generality assume $x_i^{p_1} > x_i^{p_2}$, and define a spreading factor $$\beta = \left| \frac{x_i^{c_1} - x_i^{c_2}}{x_i^{p_1} - x_i^{p_2}} \right|,$$

where $x_i^{c_1}$ and $x_i^{c_2}$ are the $i^{th}$ gene-values of offspring $c_1$ and $c_2$, respectively. The polynomial probability distribution for $\beta$, which is used to perform the contracting and expanding operations, is defined as:

$$f(\beta) = \begin{cases} 0.5(\eta_c + 1)\beta^{\eta_c} & \beta \leq 1 \\ 0.5(\eta_c + 1)\beta^{-(\eta_c + 2)} & \beta > 1 \end{cases}$$

Once $\beta$ is chosen based on the probability density function given by the above equation, $x_i^{c_1}$ and $x_i^{c_2}$ are given by $$x_i^{c_1} = \frac{1}{2}(x_i^{p_1} + x_i^{p_2}) + \frac{\beta}{2}(x_i^{p_1} - x_i^{p_2})$$

-continued $$x_i^{c2} = \frac{1}{2}(x_i^{p1} + x_i^{p2}) - \frac{\beta}{2}(x_i^{p1} - x_i^{p2})$$

While recombination operates on two or more parental chromosomes, mutation locally but randomly modifies a solution. Again, there are many variations of mutation, but these usually involve one or more changes that are made to an individual's trait or traits. In other words, mutation performs a random walk in a vicinity of a candidate solution. The example polynomial mutation used is similar to SBX, and the only difference is in the computation of polynomial probability. Instead of using genotypic distance between two parents as in SBX, the distance between a gene and its corresponding upper or lower bound, whichever is closer, is considered in computing the contracting and expanding probability distributions. In polynomial mutation, for a chromosome participating in mutation, each gene (or variable) undergoes contracting or expanding operation with a probability $p_m$.

Figure 5:
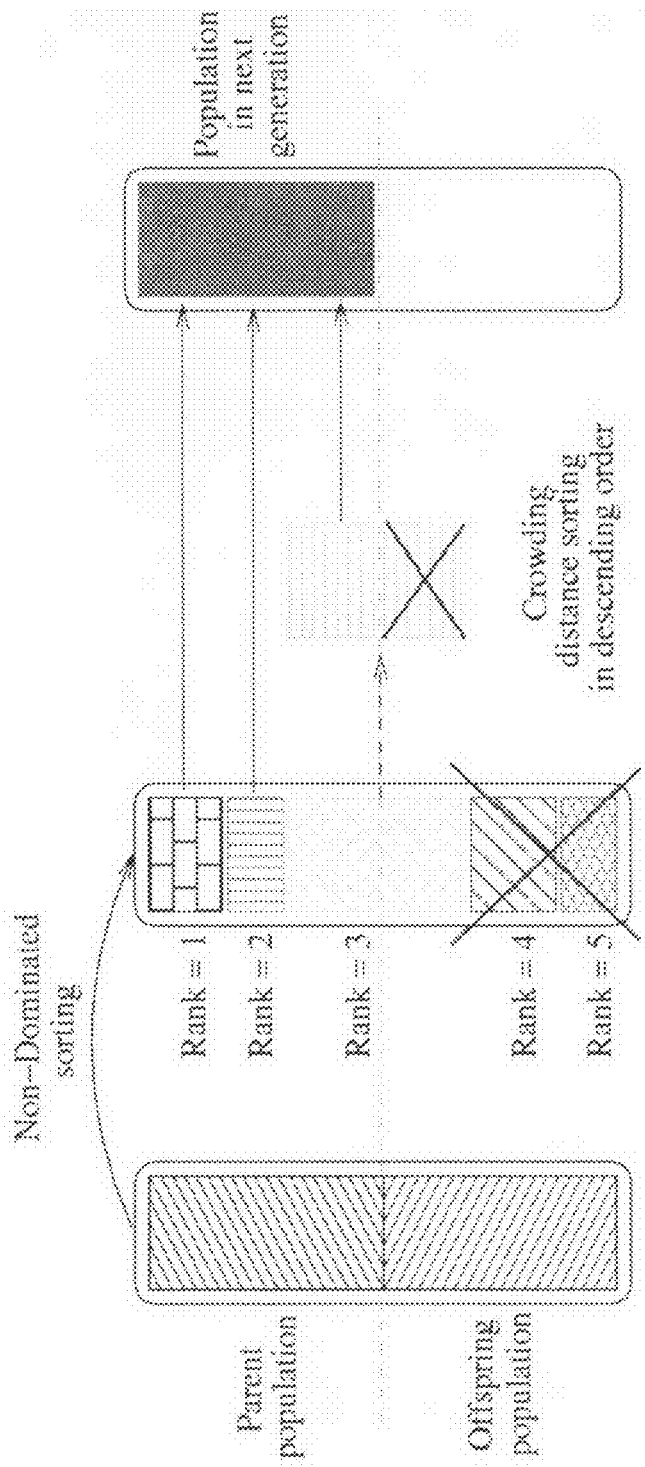
FIG. 5 shows an example elitist replacement strategy used in NSGA-II.
Figure 6A:
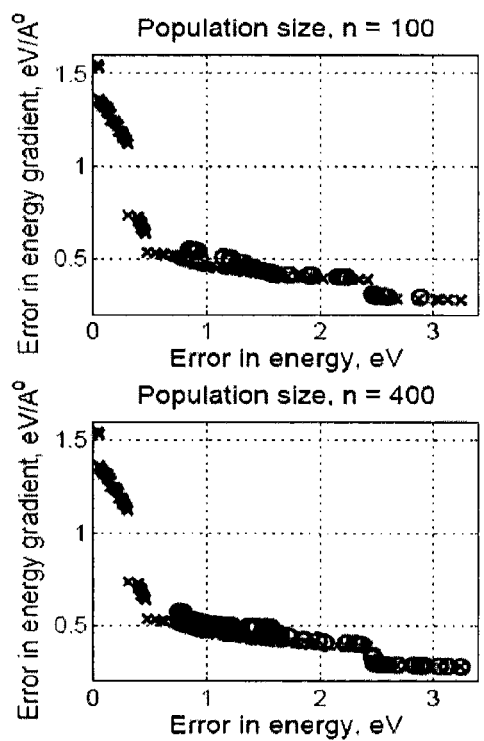
FIG. 6A-6D show an effect of different respective population sizes of n=100, 200, 400, and 800 on convergence and coverage of a multiobjective GA.
Figure 6B:
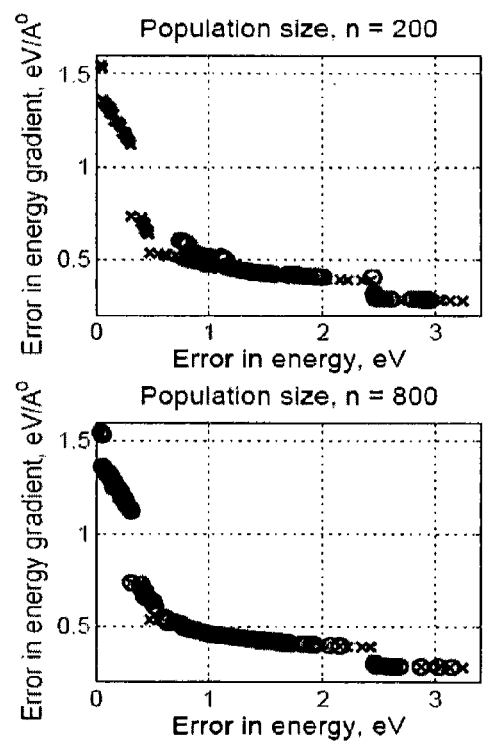
Figure 6C:
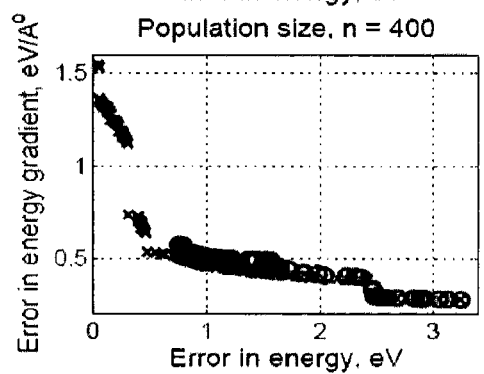
Figure 6D:
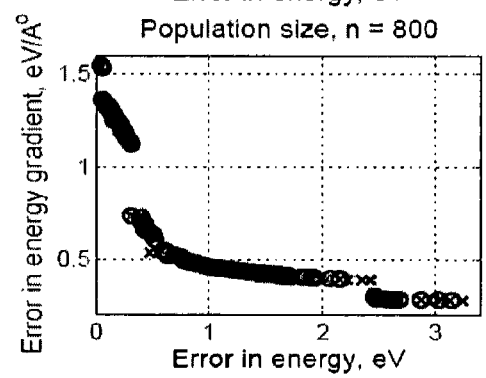

The offspring population created by selection, recombination, and mutation replaces the original parental population. An example method uses elitism where the best solutions from the parent and offspring population are retained for the next generation and used to evolve new candidate solutions. In elitist replacement, as illustrated in FIG. 5, the parent and offspring population are combined. The domination ranks and crowding distances are computed on the combined population. Individuals with increasing ranks are gradually added starting from those with the lowest rank into the new population until its size reaches to n. However, if it is not possible to add all the solutions belonging to a particular rank without increasing the population size to greater than n, individuals with greater crowding distances are preferred.

After replacement, the evolutionary process is repeated until one or more stopping criteria are met. The goal is to converge onto the Pareto-optimal solutions (the best non-dominated set). Based on convergence studies, we run NSGA-II for a maximum of 100 generations.

Results

The invention was tested with experimental simulation. The results demonstrated the effectiveness of using multiobjective genetic algorithms in rapid reparameterization of semiempirical methods for ethylene and benzene. To evaluate the results, population-sizing and run-duration requirements were estimated and then the performance of the evolutionary approach in predicting globally accurate PESs—specifically on critical and untested excited states—was compared with previously published results and with single-objective optimization.

Since the fitness calculations for ethylene are reasonably fast, the population-sizing and run duration requirements were first verified using a limited number of NSGA-II runs. To verify population-sizing requirements, five independent runs of NSGA-II with a population size of 2000 for 200 generations were run. The best non-dominated set out of those five runs was used as an approximation of the true Pareto-optimal front, which contains 61 distinct solutions. Using a population-size model for niching (Mahfoud, Population size and genetic drift in fitness sharing, Foundations of Genetic Algorithms, 3, 185-224, 1994), the population size required to maintain at least one copy of each of the Pareto-optimal points with a probability of 0.98 is computed to be 750. To verify this estimate, 10 independent runs of NSGA-II with population sizes between 50-800 were run with a fixed number of function evaluations of 80,000 for each run. The performance of NSGA-II with different population sizes is shown in FIGS. 6A-6D. As also shown in FIGS. 6A-6D, while NSGA-II with population sizes below 800 are unable to converge to the approximate Pareto-optimal front, NSGA-II with a population size of 800 discovers almost all the Pareto-optimal points.

Figure 7:
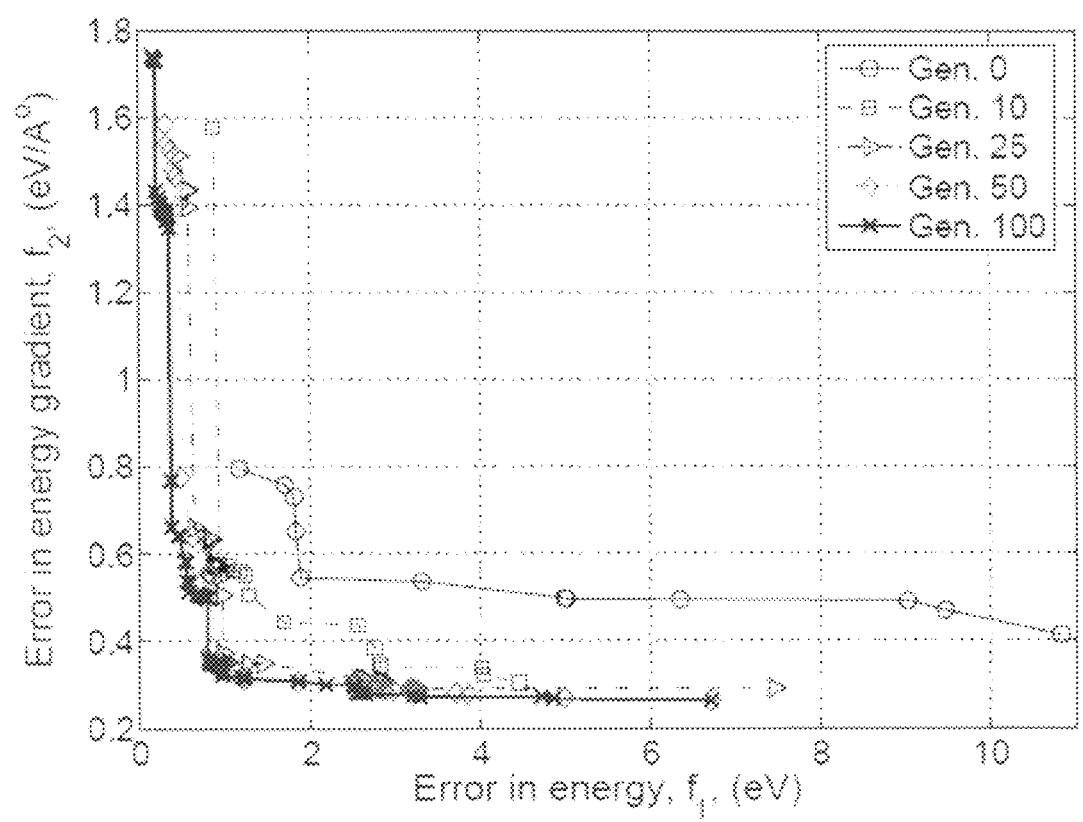
FIG. 7 shows convergence of NSGA-II for reparameterization of semiempirical parameters for ethylene.

The convergence rate of NSGA-II and the run-duration requirements for reparameterization were also considered. Specifically, ten independent runs of NSGA-II with a population size of 800 were run, and the evolution of the best non-dominated front at different generations of the evolutionary process was considered. The results are shown in FIG. 7. The results show that reasonably good quality solutions start appearing as early as the tenth generation and the solution quality improves at a steady pace until about twenty-five generations and gradually up to about 100 generations. After about 100 generations, the improvement in solution quality was found to be minimal.

Based on population-sizing and run-duration requirements in the remainder of the results a population size of 800 and run duration of 100 generations are used. Since the number of decision variables (semiempirical parameters) remains the same with different molecules involving carbon and hydrogen, the population-sizing and run-duration estimates should hold for the reparameterization of semiempirical parameters for those molecules as well. However, it should be noted that the evaluation time increases with the complexity of the molecule under consideration.

Next, the performance and efficiency of multiobjective optimization to that of single-objective optimization is compared. A weighted sum of the two objectives is taken to convert the multiple objectives into a single objective that has to be minimized:

$$f'=\alpha f_1(x)+(1-\alpha)f_2(x)$$

where $f_1$ and $f_2$ are as given in the above fitness equations, respectively, and $\alpha$ is the weighting factor. To potentially obtain different Pareto-optimal solutions, 20 different values for $\alpha$ ranging from 0.05 to 1.0 with steps of 0.05 were used. The selection, recombination, and mutation operators and their parameters were kept identical to those of the multiobjective GA.

Figure 8:
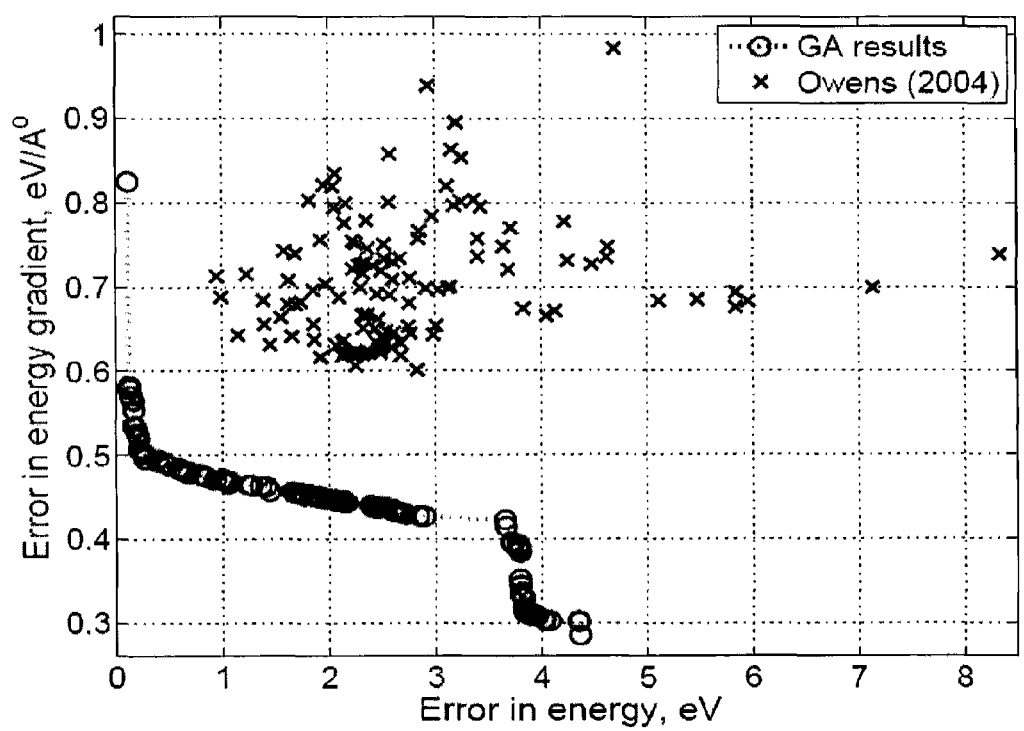
FIG. 8 shows a best non-dominated front after 100 generations for ethylene compared to prior published results.

For the multiobjective GA, a population size of 800 and a run duration of 100 generations are used. Thirty independent GA runs are conducted, and the best set of results out of the 30 runs are reported. FIG. 8 shows the best non-dominated front after 100 generations for ethylene compared to previous results (Owens, Theoretical studies of the salvation, dynamics, and photochemistry of ethylene, retinal protonated Schiff base, oligocellulose, and Gd(III) clusters, Doctoral dissertation, University of Illinois at Urbana-Champaign, Department of Chemistry, Urbana, Ill., 2004). Therefore, for the example multiobjective GA, we use a total of 800*100*30=2, 400,000 function evaluations.

Figure 9:
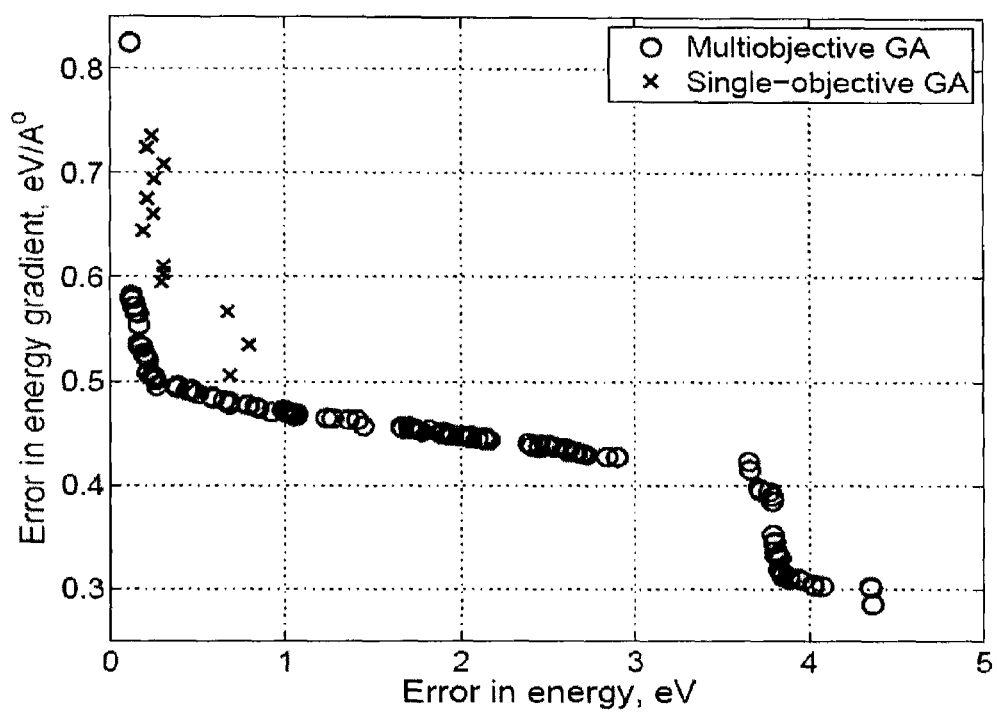
FIG. 9 shows a comparison of best non-dominated solutions obtained for ethylene via a MOGA versus multiple runs of a single-objective GA with different weights for two objectives.

For the single-objective GA, for each of the 20 values of $\alpha$, a population size of 100 and a run duration of 50 generations are used. As with multiobjective GA results, the best result out of 30 independent single-objective runs are reported. Therefore, for single-objective GA, used was a total of 100*50*30*20=3,000,000 function evaluations. That is, the single-objective GA runs use 20% more function evaluations than the multiobjective runs. Moreover, the population size and run durations settings are consistent with previous reparameterization studies using single-objective GAs. The best non-domination set obtained by the multiobjective GA is compared to results of single-objective GA in FIG. 9. The results show that the solutions obtained through multiobjective optimization are consistently superior, both in terms of error in energy and energy-gradient, than the single-objective GA results. It can be easily seen that the single-objective optimization does not yield even one solution comparable to those obtained with the multiobjective GA. Using a population size of 800 and run duration of 100 in the single-objective GA for four different values of α was tried, and the results are qualitatively similar. That is, even when single-objective GA used four times more function evaluations than the multiobjective GA, the single-objective GA failed to yield solutions comparable to those of the multiobjective GA. These results clearly demonstrate the efficiency of a multiobjective approach to reparameterization of semiempirical parameters as opposed to a single-objective optimization approach.

Next, the solution qualities provided by the best non-dominated front of NSGA-II were compared over the current published results of Owens (2004) for ethylene in FIG. 8. As shown, the solutions obtained through the example GA are significantly superior, both in terms of error in energy and energy-gradient, than those reported in Owens (2004). Specifically, the example multiobjective GA yields solutions that are 384% lower error in the energy and 32.5% lower error in the energy gradient than the previously published results. Moreover, the optimality of the parameter sets representing the best non-dominated front has been confirmed with local search and random-perturbation methods.

Figure 10:
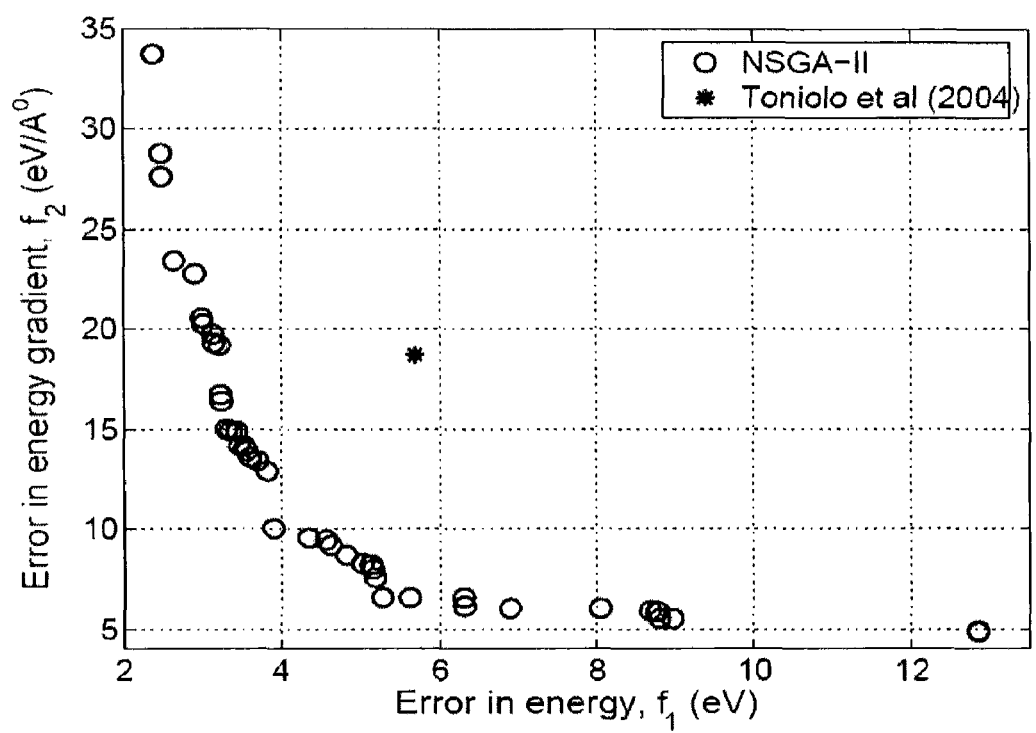
FIG. 10 shows a best non-dominated front after 100 generations for benzene compared to published results.

To verify the effectiveness of the multiobjective GA, reparameterization on benzene was also tested, which is more complex than ethylene. The results for benzene reoptimization are shown in FIG. 10. Similar to the results obtained for ethylene, the GA provides significant improvement—46% lower error in the energy and 86.5% lower error in the energy gradient—over previously reported results (Toniolo, 2004).

For ethylene, the example multiobjective GA found a total of 150 unique semiempirical parameter sets on the best non-dominated front, and for benzene, the multiobjective GA found a total of 82 unique semiempirical parameter sets on the best non-dominated front. From an optimization point of view, all the parameter sets in the best non-dominated front are equally good. However, from the chemistry perspective this may not be the case, and ultimately those semiempirical parameters that yield globally accurate potential energy surface are of interest. Therefore, it is desirable to provide parameter sets that: 1) are not sensitive to small perturbations; 2) yield accurate excited- and ground-state energies for untested, and critical configurations; and 3) yield accurate excited-state dynamics.

Since two conflicting objectives are being dealt with, one can expect that solutions with low errors in energy yield accurate configurational energies, and the solutions with low errors in energy gradient yield accurate curvature (or shape) of the potential energy surface. Of interest is selecting one or more parameter sets that not only yield accurate configurational energies, but also yield accurate shape of the potential energy surface.

A preferable property of good-quality semiempirical parameter sets is that they should be less sensitive to small perturbations. That is, if the reoptimized parameter sets are perturbed, it is desirable for the errors in the energy and energy gradient to be similar to those of the Pareto-optimal parameter sets. A sensitivity or stability analysis of the parameter sets can be performed, for example, by considering the errors in energy and energy gradient of randomly perturbed parameter sets around the Pareto-optimal parameter sets. If the error in energy and energy-gradient of the perturbed parameter sets are greater than some threshold, then they are deemed as sensitive. The question then becomes the value of these thresholds.

Standard parameter sets such as PM3 have traditionally been held as robust or stable. Therefore, perturbing the PM3 parameter set and analyzing the errors in energy and energy-gradient of the parameter sets should provide an idea of what the threshold values should be for determining the stability of the Pareto-optimal parameter sets. The PM3 parameter sets were randomly perturbed, and over 600 perturbed parameter sets are created, such that the parameter values of the perturbed parameter sets are within 2% of the PM3 set. That is, the relative distance between every semiempirical parameter in the perturbed set and the PM3 set is less than 0.01:

$$\left| \frac{x_i' - x_i}{x_i} \right| \leq 0.01, \quad i = 1, 2, \ldots 11.$$

Here $x_i$ and $x_i'$ are the values of the $i^{th}$ parameter in the PM3 set and perturbed parameter set, respectively.

Figure 11:
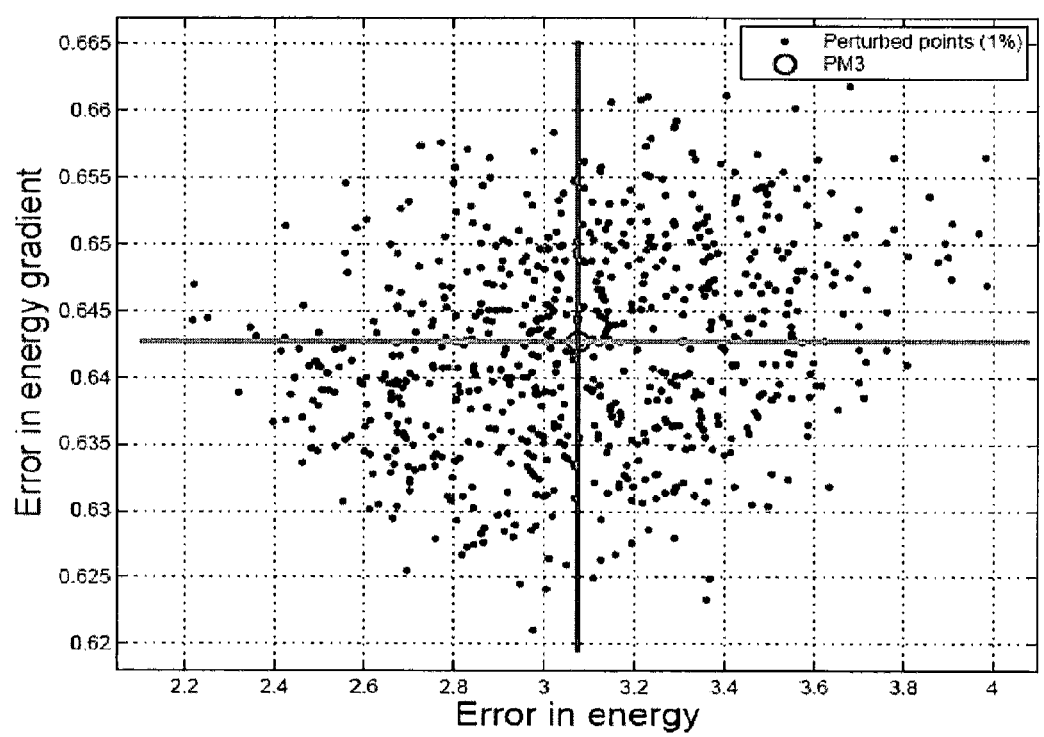
FIG. 11 shows sensitivity of PM3 parameter set to random perturbation, including errors in energy and energy gradient for 606 randomly perturbed parameter sets.

The errors in energy and energy gradient for each of the perturbed parameter sets are computed and are plotted in FIG. 11. The results in FIG. 11 show that the RMS deviation in error in energy of the perturbed points from that of PM3 is 0.99 eV. Similarly, the RMS deviation in error in energy gradient of the perturbed points from that of PM3 is 0.023 eV/A°. Therefore, threshold values of 0.99 and 0.023 are used for assessing stability of the Pareto-optimal sets.

One advantage of using genetic algorithms is that one has a population of candidate solutions that can be used to perform an on-line sensitivity analysis of the optimal semiempirical parameter sets. Performing such a sensitivity analysis not only reduces the number of acceptable reoptimized parameter sets, but is also more efficient and reliable than a manual stability/sensitivity analysis. Thus, such an analysis is performed, and along with saving the Pareto-optimal semiempirical parameter set, for each of the Pareto-optimal solutions maintained is a list of parameter sets visited during the GA process that are within 2% from that Pareto-optimal solution. The RMS deviation in errors in energy and energy gradient can then be computed between the Pareto-optimal solution and the parameter sets around it. If both the RMS deviation in error and energy gradient is less than their respective threshold, then the Pareto-optimal solution is labeled as being stable. On the other hand, if either of the deviations is greater than the threshold, then the Pareto-optimal solution is labeled as sensitive.

Figure 13A:
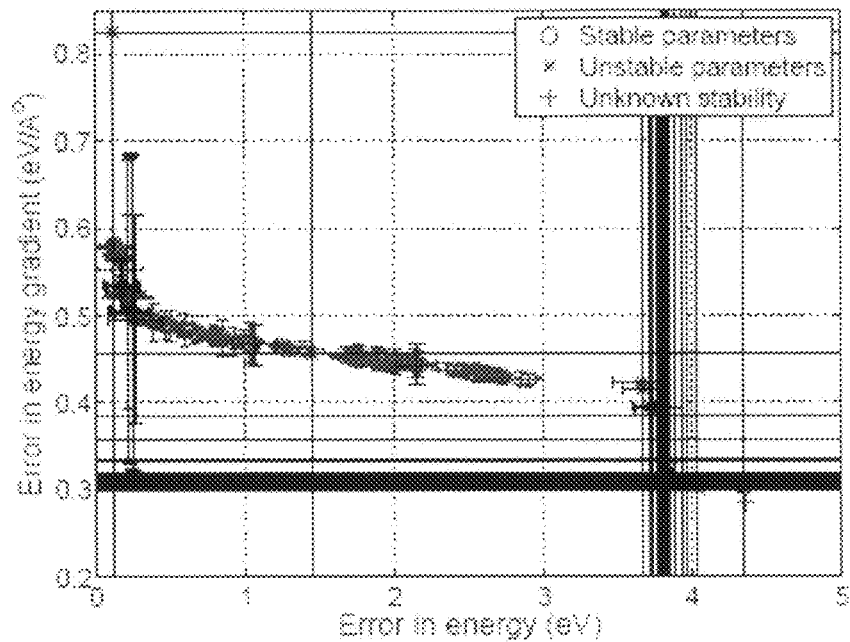
FIGS. 13A and 13B show RMS deviations in error in energy and energy gradient for each of Pareto-optimal solutions, and stable Pareto-optimal solutions, respectively.

As shown in the histogram of FIG. 12A, for a majority of the Pareto-optimal solutions, there are sufficient parameter sets within 2% to yield acceptable measure of their sensitivity. Indeed, the GA population contains less than 5 parameter sets with 2% of only 6 Pareto-optimal solutions. On an average there are 95 (and a maximum of 495) parameter sets within 2% of the Pareto-optimal solutions. FIGS. 12B and 12C also show the RMS deviations of error in energy and error in energy gradient between the Pareto-optimal solutions and the corresponding neighboring parameter sets. The RMS deviation in energy and energy gradient for each of the Pareto-optimal solutions is shown in FIG. 13A. The online sensitivity analysis reveals that 44 out of 150 Pareto-optimal solutions have either RMS deviation in error or energy or RMS deviation in error in energy gradient or both are greater than their respective threshold and therefore are sensitive. The results also show that 100 out of 150 Pareto-optimal solutions have both RMS deviations in errors in energy and energy gradient that are below the threshold and thus are considered stable or less sensitive to small perturbations in the parameter values.

Figure 13B:
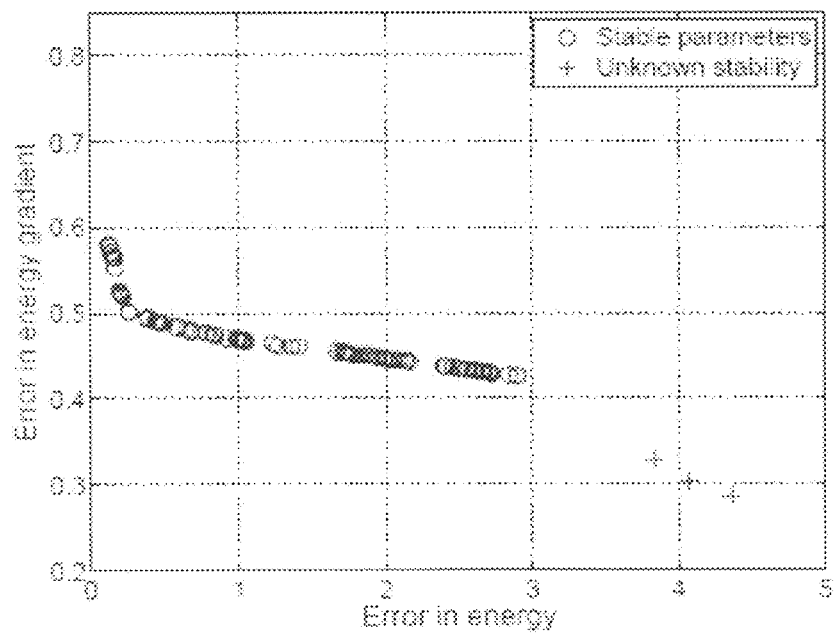

The parameter sets that are found to be stable via the online sensitive analysis are shown in FIG. 13B.

Figure 14:
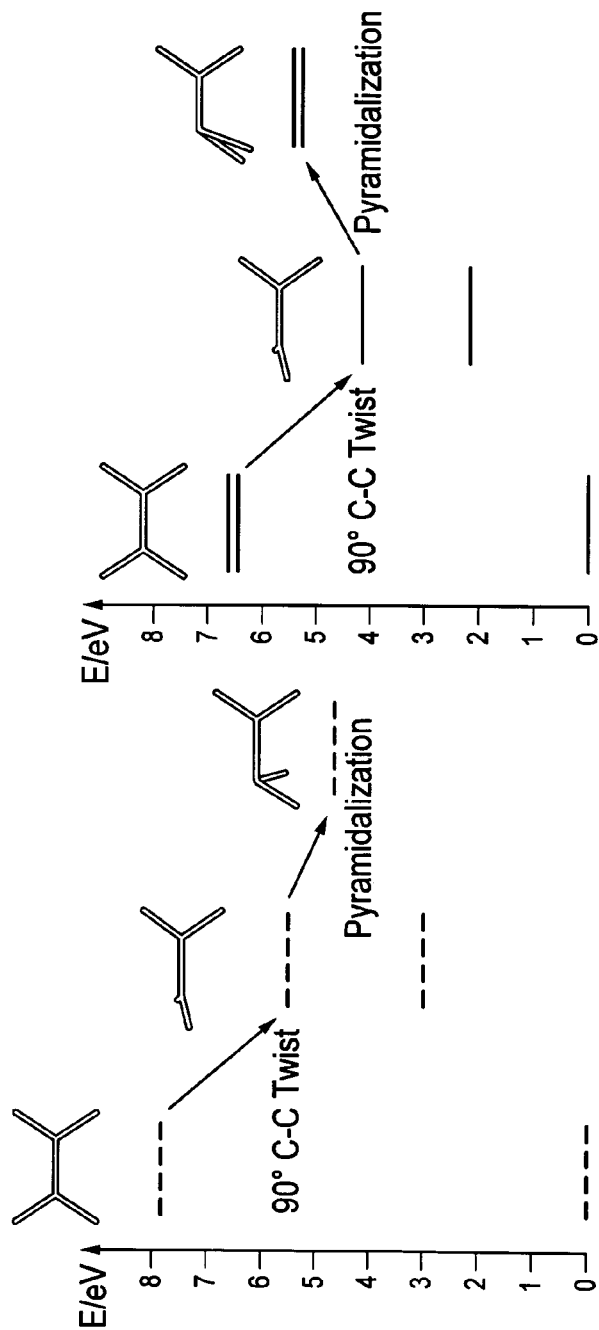
FIG. 14 shows energy levels of ethylene at various geometries: planar, twisted, and pyramidalized from ab initio calculations and from PM3 and AM1 calculations, respectively.

Consider now solutions obtained through the example GA and evaluate their results on energetic calculations for a set of ethylidene geometries for which they were not reoptimized. Previous ab initio work has shown that in addition to the twisting coordinate, a coordinate involving the pyramidalization of one of the carbons is also important. Ultrafast pump-probe experiments have shown a very fast excited state lifetime for ethylene. Recent theoretical works suggest that the twisted-pyramidalized geometry is responsible for the fast non-radiative transfer to the ground state through a conical intersection. That is, considering certain salient properties of cis-trans isomerization of ethylene, the ground state for ethylene is a planar structure as shown in FIG. 14. When it is excited, the carbon-carbon bond twists 90° and decreases in the energy gap from 7.8 eV to 2.5 eV. The twisted geometry, however, is not an excited state minimum but a saddle point with respect to pyramidalization of one of the carbon atoms. As shown in FIG. 14, using the PM3 and AM1 parameters, however, the pyramidalized geometry is actually higher in energy than the purely twisted geometry on the excited state, which is in direct contrast to the results of experiments and high level calculations.

Figure 15A:
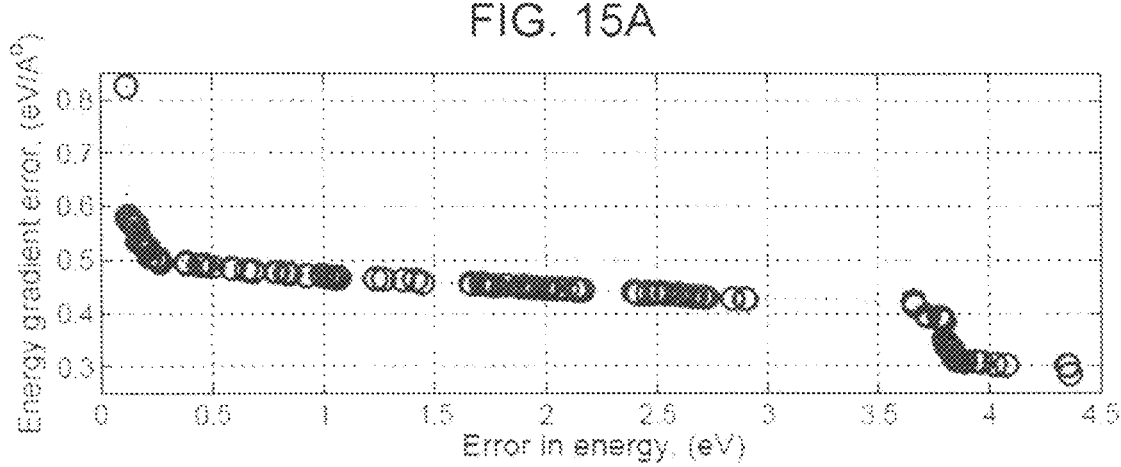
FIG. 15A shows best non-dominated parameter sets obtained via multiobjective GA.
Figure 15B:
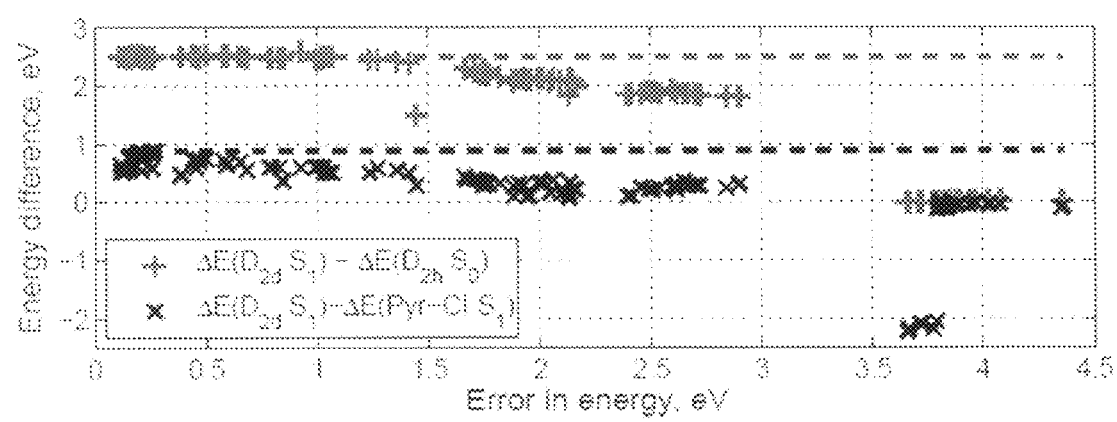
FIG. 15B shows energy differences between planar and twisted geometries, and between twisted and pyramidalized geometry.

Two significant energetics are considered, and results are compared, as shown in FIGS. 15A and 15B:

1) Energy differences between planar ethylene (ground state, $S_0$ minimized $D_{2h}$) and twisted geometry ($S_1$ minimized $D_{2d}$), ideal value for which is 2.28 eV as calculated by ab initio methods. If the energy difference between the planar and twisted geometry is less than zero, then the excited state minimum would be the planar structure, which is erroneous. In other words, for good parameter sets, the energy difference between the planar and twisted geometry should be greater than zero, preferably around 2.28 eV.

2) Energy differences between the twisted geometry ($S_1$ minimized $D_{2d}$) and pyramidalized structure, ideal value for which is 0.88 eV as calculated by ab initio methods. As shown in FIG. 14, the standard semiempirical parameter sets do not capture this feature, and therefore this energetics is one of the critical phenomena in determining the quality of the reoptimized parameter sets. If the energy difference between the twisted geometry and the pyramidalized structure is less than zero, then the excited state minimum would be the twisted geometry (as predicted by standard parameter sets), which is inconsistent with ab initio and experimental results. Therefore, for good parameter sets, the energy difference between the twisted and pyramidalized geometries must be greater than zero, preferably around 0.88 eV.

Figure 16A:
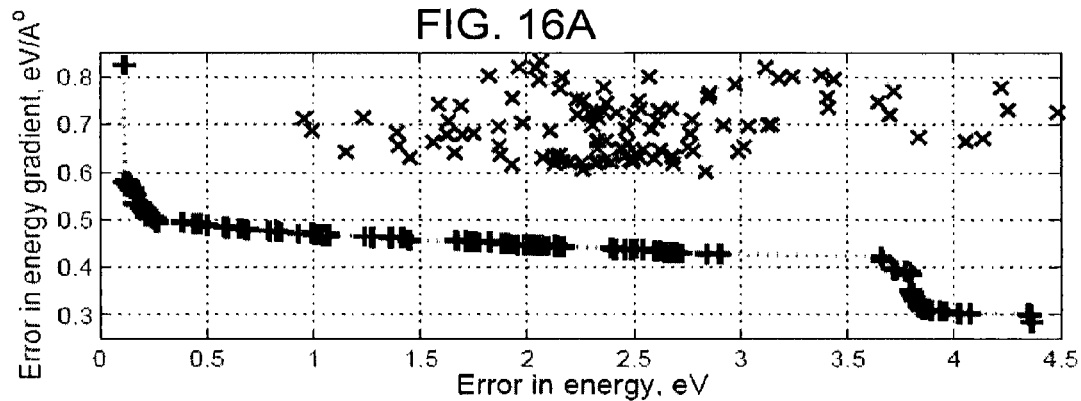
FIG. 16A shows best non-dominated sets and a previous solution set.
Figure 16B:
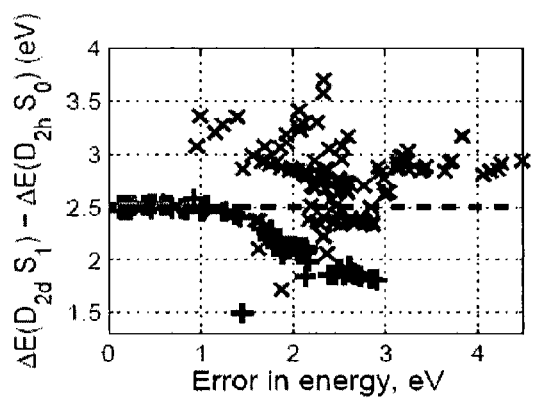
FIG. 16B shows an energy difference between planar and twisted geometries.
Figure 16C:
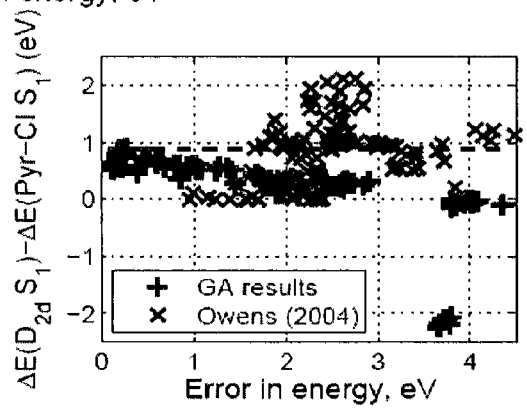
FIG. 16C shows an energy difference between twisted and pyramidalized geometry.

Among the Pareto-optimal solutions, one would expect those parameter sets with lower error in energy to be able to yield accurate energetics of untested configuration as opposed to those with higher error in energy. The energy differences between planar and twisted geometry, and twisted geometry and planarized structure, for both the best non-dominated sets are shown in FIG. 15 along with the corresponding solutions. FIGS. 15A and 15B show that the Pareto-optimal solutions with error in energies less than 1.5 eV yield near ideal energies for both excited-state transitions. Moreover, as shown in FIGS. 16A-16C, the results obtained via multiobjective GA have been shown to be clearly superior to prior results. More importantly, the example multiobjective GA optimized parameter sets correctly identify the lowest-energy excited state as the pyramidalized structure as opposed to standard semiempirical parameter sets and some of the previously reported reparameterized sets.

The final requirement of good parameter sets from a chemistry perspective is that they yield accurate reaction dynamics simulations. It should be noted that the dynamics are controlled by the shape of the PES. Since error in energy gradient gives a measure of the accuracy of the PES, it is reasonable to expect that Pareto-optimal solutions with lower error in energy gradient yield accurate dynamics over those with higher error in energy gradient. This expectation was validated by dynamics calculations.

Specifically, excited state lifetime was considered, and the average time for half the population to transfer from $S_1$ (excited state, pyramidalized) to $S_0$ (ground state, planar) following photoexcitation of the gas-phase molecule was computed. This phenomenon has been extensively studied using ab initio simulations. The AIMS simulations used multi-reference configuration interaction (MRCI) electronic wavefunctions within a double zeta basis set. The simulations did not include Rydberg basis functions, the nuclear dynamics is followed for 0.5 picoseconds, and the total dynamics is represented by averaging over results obtained using 10 different representations of the initial wavefunction. Overall, approximately 100 nuclear basis functions are spawned during the simulation time. The ab initio results indicate that the average time for half the population to transfer from $S_1$ to $S_0$ is 180±50 fs.

Figure 17:
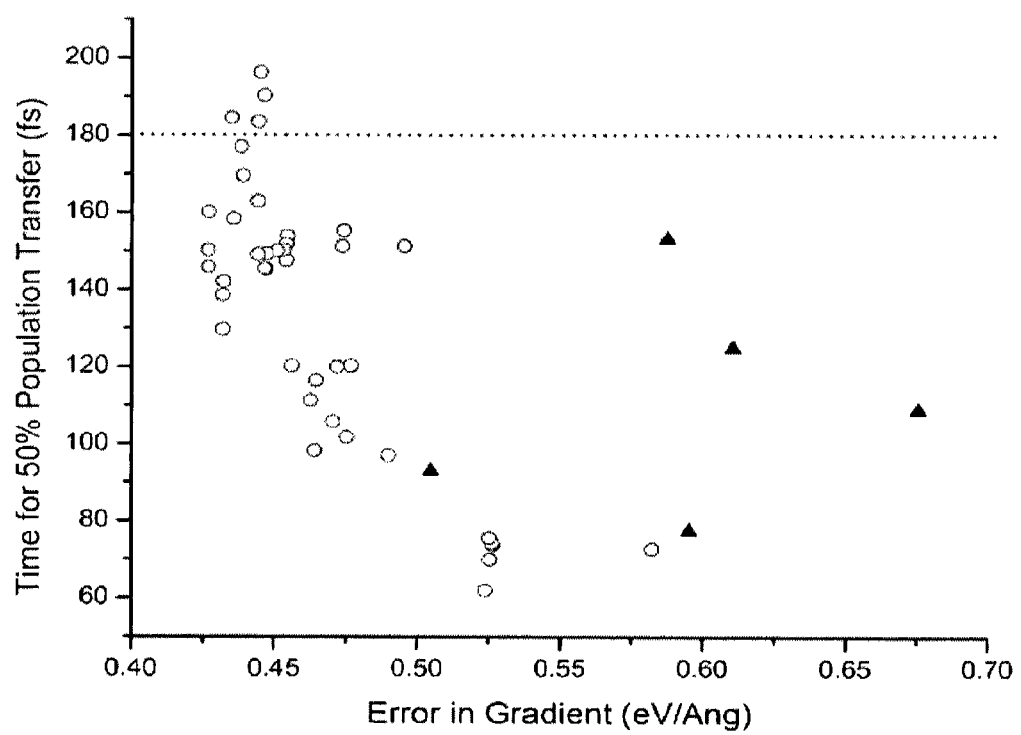
FIG. 17 shows the average time for half the population to transfer from $S_1$ (excited state, pyramidalized) to $S_0$ (ground state, planar) following photoexcitation of the gas-phase ethylene for the stable Pareto-optimal semiempirical parameters.

The dynamics simulations are computed for each of the stable Pareto-optimal solutions and compared to the ab initio simulation results. The dynamics results are averaged over 50 independent dynamics simulations and are plotted as a function of error in energy gradient in FIG. 17. The results show that most of the stable Pareto-optimal solutions—especially those with lower error in energy gradient—yield near ideal, ab initio quality dynamics results. Moreover, the dynamics simulation results for the best solutions obtained via single-objective optimization are significantly worse than those obtained via multiobjective optimization. In essence, the dynamics simulation results clearly show that the majority of the stable Pareto-optimal solutions—specifically 85 out of 100—yield dynamic results in agreement with ab initio simulations.

Figure 18:
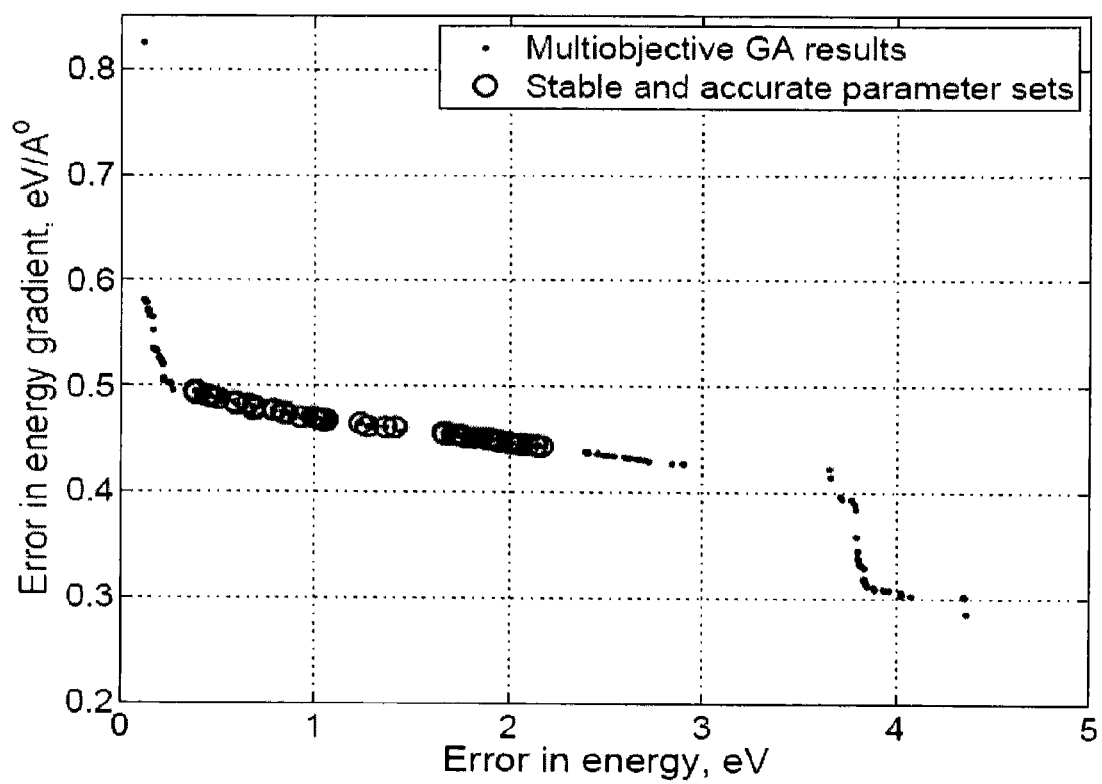
FIG. 18 shows a subset of Pareto-optimal solutions for ethylene that are stable to small perturbations, yield accurate energetics for untested, yet critical configurations, and yield dynamics with ab initio accuracy.
Figure 19A:
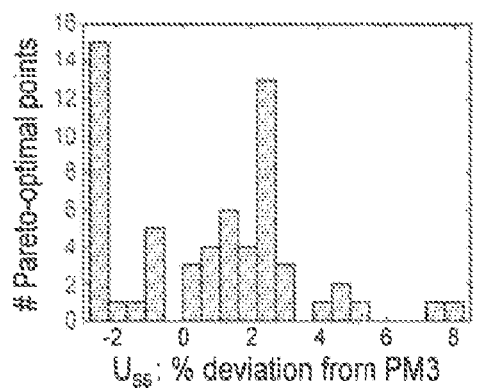
Figure 19B:
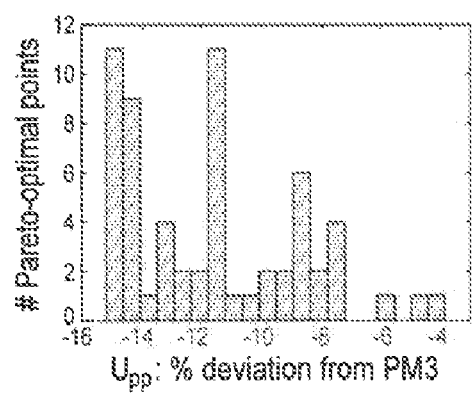
Figure 19C:
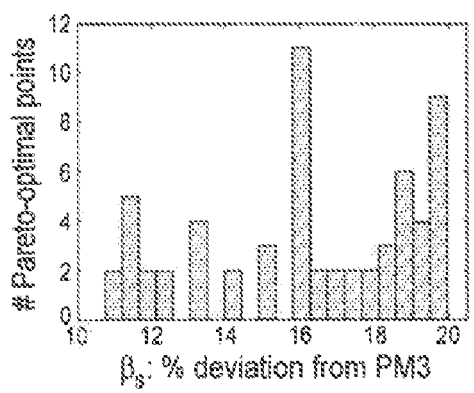
Figure 19D:
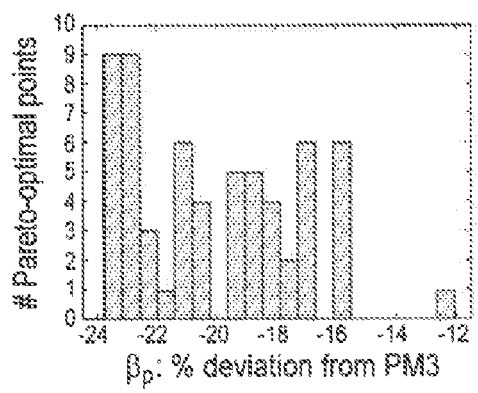
Figure 19J:
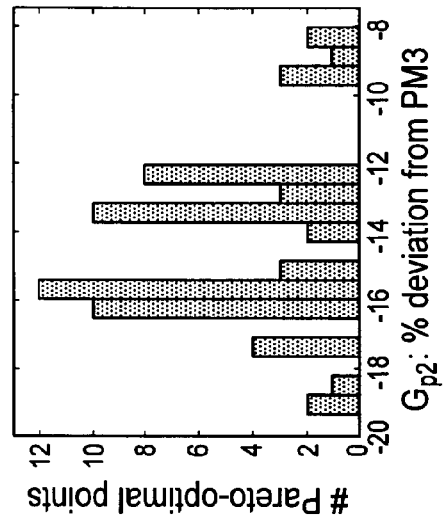
Figure 19I:
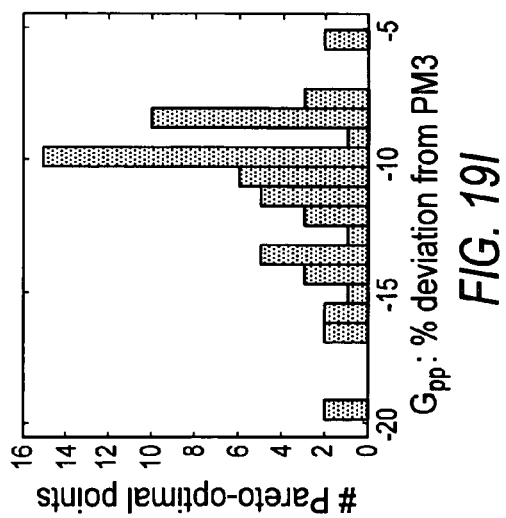
Figure 19K:
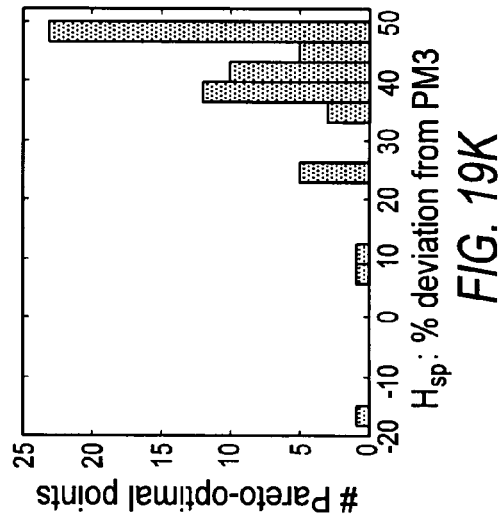

The above results clearly show that multiobjective GA yields multiple semiempirical parameter sets that 1) are stable to small perturbations, 2) yield accurate (indeed, near ideal) energetics for untested, yet critical excited-state configurations, and 3) yield dynamics with ab initio accuracy. The subset of Pareto-optimal solutions that are stable and produce accurate energies and dynamics are shown in FIG. 18. Combining the results from online sensitivity analysis, energetics tests, and dynamics simulations, reveals that out of the 150 parameter sets in the Pareto-optimal front, 61 parameter sets are stable and yield accurate configurational energies and dynamics. Interestingly, parameter sets that are stable and yield accurate energies and dynamics are not on and around the nose of the Pareto front as one might expect, but are slightly to the right of the Pareto front. This is because a slight increase in error in energy leads to an improvement in error in energy gradient, which controls the accuracy of dynamics.

It should also be noted that similar to ethylene, results for benzene also show that while the standard semiempirical sets yield inaccurate dynamics, the example multiobjective GA optimized parameter sets yield results consistent with experiments and ab initio computations. For example, the newly optimized parameter sets predict an $S_2$ lifetime of 100 fs, in agreement with previous experiment.

The multiobjective optimization of the semiempirical parameters for ethylene resulted in 61 different optimal parameter sets. FIGS. 19A-19K depict histograms of the deviation of the 11 semiempirical values from their corresponding PM3 values. The results show that the parameter values, with the exception of $\zeta_p$, are very diverse. Understanding the relationship between these optimal, stable, and accurate semiempirical parameters can yield insights into important energy relations for the given molecule. In addition to yielding physical insights into the excited-state energetics, if we can determine the relationships between the semiempirical parameters, we would have interpretable semiempirical methods.

Another advantage of using multiobjective GA is that the Pareto-optimal solutions can be mined to automatically discover the relation between semiempirical parameters. The multiple reoptimized parameter sets of semiempirical methods yield globally correct potential energy surfaces. Therefore, the interactions among the parameters can contain important information about the molecules. Understanding these key interactions is helpful to developing a robust multiscaling method. Traditional clustering techniques, the model-building process of Bayesian optimization algorithm, and/or symbolic regression via genetic programming can be used to understand the parameter interactions. In a nonlimiting example, using the optimal, stable, and accurate parameter-set data, the relationship between the semiempirical parameters can be symbolically regressed via genetic programming. Accordingly, the 61 Pareto-optimal parameter sets that 1) are stable to small perturbations, 2) yield accurate configurational energies, and 3) yield ab initio quality excited-state dynamics are selected. The data is normalized using a z-score score $$x'_i = \frac{x_i - \overline{x}_i}{s_{x_i}}$$

where $\overline{x}_i$ and $s_{x_i}$ are the sample mean and variance of the $i^{th}$ semiempirical parameter, respectively. The objective then is to determine the functional relationship between each of the 11 semiempirical parameters as a function of the rest of the 10 parameters. For example, we use GP to evolve a functional relationship between $U_{ss}$ in terms of $U_{pp}$, $\beta_s$, $\beta_p$, $\zeta_s$, $\zeta_p$, $G_{ss}$, $G_{sp}$, $G_{pp}$, $G_{p2}$ and $H_{sp}$.

The normalized data is used to evolve relationships between the semiempirical parameters via GP. The following function set $F=\{+,-,*,/,^{\wedge},\exp\}$ is used for all the runs. The terminal set contains an ephemeral random constant and all the semiempirical parameters except the one for which we want to discover the functional relationship. For example, if we want to find the relationship between $U_{ss}$ and the rest of the semiempirical parameters, then the terminal set would consist of $T=\{U_{pp},\beta_s,\beta_p,\zeta_s,\zeta_p,G_{ss},G_{sp},G_{pp},G_{p2},H_{sp},\Re\}$. The output of the candidate program is the normalized value of a semiempirical parameter.

The fitness of a solution is computed as the root mean square error (RMSE) between the predicted and Pareto-optimal value of the semiempirical parameter for which we are evolving the candidate program. In all GP runs, a population size of 1000 and run duration of 100 generations were used. For each semiempirical parameter, over 100 independent GP runs were computed. The best evolved regression function for each of the independent runs is then simplified using the symbolic math toolbox in MATLAB. The coefficients are then optimized using either linear or non-linear regression methods. Generally, the results were:

For $U_{ss}$, 37 out of 113 independent GP runs suggest that $U_{ss}$ is linearly proportional to $U_{pp}$, $G_{p2}$, and $\beta_s$. Moreover, all the independent runs suggest a linear relationship between $U_{ss}$ and $U_{pp}$, which is in agreement with previously published analysis.

For $U_{pp}$, 76 out of 113 independent GP runs suggest that $U_{pp}$ is linearly proportional to $\beta_p$ and $G_{sp}$. Additionally, 21 independent GP runs suggest that $U_{pp}$ is linearly proportional to $U_{ss}$ and $G_{p_2}$. Finally, the most accurate, least-complex relationship is a linear combination of the two most frequently evolved symbolic expressions.

For $\beta_s$, 38 out of 113 independent GP runs suggest that $\beta_s$ is linearly proportional to $G_{ss}$ and $G_{p_2}$. Moreover, all the independent GP runs indicate a relationship between $\beta_s$ and $G_{ss}$.

For $\beta_p$, 28 independent GP runs suggest a linear relationship between $\beta_p$ and $G_{ss}$ and $G_{pp}$. Additionally, 21 independent runs suggest a linear relationship between $\beta_s$ and $U_{pp}$ and $G_{sp}$.

For $\zeta_s$, 16 independent GP runs suggest that $\zeta_s$ is related to the product of $\zeta_p$, $G_{pp}$, and $U_{ss}$. However, the high RMS error coupled with the majority of independent GP runs yielding very diverse relationships for $\zeta_s$ suggest that $\zeta_s$ does not have a strong relationship with other semiempirical parameters.

For $\zeta_p$, 52 independent GP runs suggest that $\zeta_p$ is directly proportional to $\zeta_s^2 \beta_s$. Moreover, all independent GP runs indicate a relationship between $\zeta_p$ and $\zeta_s$.

For $G_{ss}$, 22 independent GP runs reveal a linear relationship between $G_{ss}$, $G_{p_2}$ and $\beta_s$, and 14 independent GP runs reveal a relationship between $G_{ss}$, $G_{p_2}$ and $\zeta_p$. Moreover, a majority of the independent GP runs reveal a relationship between $G_{ss}$ and $G_{p_2}$.

For $G_{sp}$, 75 independent runs suggest that $G_{sp}$ is linearly proportional to $\beta_p$, and $U_{pp}$. Moreover, all the independent runs consist of the similar relationship between $G_{sp}$, $\beta_p$ and $G_{sp}$.

For $G_{pp}$, 90 independent GP runs reveal that $G_{pp}$ is linearly proportional to $\zeta_p$, $\beta_p$, and $G_{p_2}$. Indeed the best solutions evolved in all the GP runs contain the above relationship.

For $G_{p_2}$, 29 independent GP runs suggest that $G_{p_2}$ is linearly proportional to $G_{ss}$ and $U_{pp}$, and 20 independent runs suggest that $G_{p_2}$ is linearly proportional to $G_{ss}$ and $\zeta_s$. Furthermore, all independent GP runs suggest that $G_{p_2}$ depends on $G_{ss}$.

For $H_{sp}$, 28 independent GP runs reveal that $H_{sp}$ is related to $G_{p_2}$ and $G_{pp}$. More importantly, all the runs indicate that $H_{sp}$ is related to $G_{pp}$ and $G_{p_2}$, which is in agreement with previously published analysis.

Though particular example methods are described herein, one of ordinary skill in the art will appreciate that the invention is not limited to the methods used in these examples, and that various modifications are possible. For instance, an example method uses fixed evolutionary operators that do not adapt linkage, which may limit scalability in reparameterizing semiempirical methods for other complex molecules. One class of evolutionary algorithms that might be particularly effective—especially for complex molecules—may be competent genetic algorithms. Efficient and competent genetic algorithms may be used, such as but not limited to the extended compact genetic algorithm (eCGA), to reoptimize the parameter sets needed to define a useful semiempirical potential for different classes of molecules to yield globally accurate PES, excited states, and geometries based on a very limited learning data from quality ab initio and/or experimental data. Similarly, decomposition-based design approaches are possible to help successfully design competent and efficient genetic algorithm operators. Significantly, such reoptimization preferably is massively multimodal and involves conflicting and competing objectives, such as minimizing differences between calculated and predicted energies, gradients of energies, and stationary-point geometries.

Additionally, the example optimization method described tunes a potential, but it is also contemplated according to alternative embodiments to evolve empirical potentials using genetic programming (GP). Thus, even if the functional form of the semiempirical process is unknown, it may be evolved without problem knowledge. Ab initio methods compute the potential energy surfaces from scratch and are highly accurate, but are prohibitively expensive even for small systems. GP may be used to regress symbolically the PES from a limited set of directly calculated points on the PES using an accurate method. Such GP regression provides an inline function for increasing number of active configurations (or complexity) as a machine-learned replacement to the "look-up table" approach. Multiscale modeling requires only relevant information at the appropriate scales.

In an example of this alternative embodiment, an inline semiempirical function may be represented by a GP tree generated from a function set of various primitive functions and a terminal set. The primitive functions and/or terminal set may be selected at least partially based on problem knowledge, though this is not necessary. An ephemeral random constant may also be used as part of the terminal set. Given the appropriate fitness function (or functions) for evaluating quality of the tree (e.g., error between predicted and calculated energy and/or energy gradient), a semiempirical function may be evolved. Appropriate GP techniques may be employed (e.g., tournament selection, subtree crossover, subtree mutation, point mutation), as would be appreciated by those of ordinary skill in the art. Further, advanced GP features (such as, but not limited to, constrained syntactic structures, automatically defined functions, etc.) may be used. Given this approach, it is possible to use a machine-learning method to determine accurately, and with little information, complete details of a potential energy surface and output.

Generally, multiobjective genetic algorithms may be used according to example embodiments of the present invention in multiscaling simulations of excited state dynamics in photochemistry. More particularly, MOGAs have been used to bridge high-level quantum chemistry and semiempirical methods to provide an accurate representation of complex molecular excited-state and ground-state behavior, well beyond previous attempts, or expectation of human experts, and a dramatic reduction (from about 100 to 1000 times) in computational cost. Rapid reparameterization of semiempirical methods not only eliminates the need for a full-fledged ab initio dynamics simulation, which is prohibitively expensive for large molecules, but also eliminates drawbacks of semiempirical methods that use standard parameter sets and can yield unphysical dynamics. The results show that the evolutionary approach provides significantly better results—for example, up to 384% lower error in the energy and 86.5% lower error in the energy gradient—than those of conventional methods. Furthermore, example methods provide a large number of parameter sets, all of which yield globally accurate PESs and physical dynamics.

For multiscaling excited-state direct dynamics of photochemistry, it is useful to obtain high-quality reoptimized semiempirical parameters that are transferable to other complex molecules containing similar properties as ethylene and benzene. For example, the reoptimized parameter sets for ethylene and benzene may be transferable to other molecules. The MOGA results produce transferable potentials—that is, parameters from one molecular system can be used for similar systems, analogous to use of building blocks in genetic algorithms. As a nonlimiting example, parameters from one molecular system can be used for similar systems, such as ethylene parameters to simulate benzene (and vice versa). Optimized semiempirical parameters of a small number of relatively simple molecules can be used to predict accurately the behavior of large complex molecules. Such transferability may allow, for example, GAs to enable the fast, accurate simulation of complex molecules from a standard GA-tuned database. This allows, as a nonlimiting example, direct simulation of photoinduced cis-trans isomerization in molecules such as (but not limited to) stilbene and azobenzene, as well as energy transfer in dendrimeric molecules. Furthermore, this opens up the possibility of accurate simulations of photochemistry in complex environments such as proteins and condensed phases, providing new ways for modeling and designing chemicals.

The GA-discovered potentials inherit the accuracy of the ab initio data, permit simulations to orders of magnitude larger time scales (e.g., picoseconds) than that believed currently possible by ab initio methods (e.g., femtoseconds), even for simple molecules, and exhibit transferability in initial tests. A MOGA optimization approach, according to preferred embodiments of the present invention, provides an enabling technology to simulate successfully, within a reasonable time frame and with sufficient accuracy, complex, multiscale biological, chemical, and materials problems that are ubiquitous in science and engineering, and thus impact one's ability to address critical biophysical simulations of, for example, vision and photosynthesis, and for automated design of pharmaceuticals and functional materials. Applications include, but are not limited to, computational materials, chemistry, physics, biochemical, and pharmaceutical analysis and design.

Methods and systems according to the present invention may be applicable to simulations of other physical, chemical, biochemical, and/or biological events. For example, optimization, artificial intelligence and machine learning methods such as genetic programming (GP) may be used to provide more accurate and efficient solutions for simulating or predicting dynamics of materials-related events, such as molecular dynamics and physical dynamics.

Embodiments of the present invention are directed to methods and program products for tuning or evolving reaction simulations using optimization methods, and for simulating reactions. Those knowledgeable in the art will appreciate that embodiments of the present invention lend themselves well to practice in the form of computer program products. Accordingly, it will be appreciated that embodiments of the present invention may comprise computer program products comprising computer executable instructions stored on a computer readable medium that when executed cause a computer to undertake methods according to the present invention, or a computer configured to carry out such methods. The executable instructions may comprise computer program language instructions that have been compiled into a machine-readable format. The computer-readable medium may comprise, by way of example, a magnetic, optical, signal-based, and/or circuitry medium useful for storing data. The instructions may be downloaded entirely or in part from a networked computer. Also, it will be appreciated that the term "computer" as used herein is intended to broadly refer to any machine capable of reading and executing recorded instructions. It will also be understood that results of methods of the present invention may be displayed on one or more monitors or displays (e.g., as text, graphics, charts, code, etc.), printed on suitable media, stored in appropriate memory or storage, etc. Other embodiments of the invention include systems for tuning or evolving reaction simulations using optimization methods and for simulating reactions, with an example being a processor-based system capable of executing instructions that cause it to carry out a method of the invention. It will accordingly be appreciated that description made herein of a method of the invention may likewise apply to a program product of the invention and/or to a system of the invention. Resulting parameter set and optimized functional forms are also embodiments of the present invention.

While various embodiments of the present invention have been shown and described, it should be understood that other modifications, substitutions, and alternatives are apparent to one of ordinary skill in the art. Such modifications, substitutions, and alternatives can be made without departing from the spirit and scope of the invention, which should be determined from the appended claims.

Various features of the invention are set forth in the appended claims.

What is claimed is:

1. A method for tuning a semiempirical process for predicting energy for different molecular configurations, the method comprising:
    determining an energy value and an energy gradient for each of a plurality of molecular configurations using an accurate method and providing the energy value and the energy gradient in a computer;
    using the computer to optimize a functional form of the semiempirical process using said determined energy values and energy gradients via multiobjective optimization, wherein the functional form relates one or more parameters to energy values and energy gradients; and storing the optimized functional form in the computer.

2. The method of claim 1, wherein said optimizing comprises:
    using the computer to optimize the one or more parameters based on the determined energy values and the energy gradients;
    wherein said optimizing provides a plurality of optimized sets of parameters.

3. The method of claim 2, wherein said optimizing comprises:
    providing, in the computer, a multiobjective evolutionary algorithm having at least two fitness functions;
    wherein one of the fitness functions compares predicted energy values derived from the one or more parameters and accurate energy values based on said determining an energy value;
    wherein another of the fitness functions compares predicted energy gradients derived from the one or more parameters and accurate energy gradient values based on said determining an energy gradient.

4. The method of claim 3, wherein at least one of the at least two fitness functions compares predicted geometry derived from the one or more parameters and an accurate geometry.

5. The method of claim 3, wherein said optimizing further comprises:
    initializing a population of solutions, wherein each of the solutions comprise a set of the one or more parameters;
    using the computer to determine a fitness for said initialized population of solutions based on said at least two fitness functions;
    using the computer to select a mating pool of solutions from among said initialized population of solutions, wherein said selecting is based on non-domination of one solution versus another solution;
    using the computer to produce offspring from said selected mating pool of solutions.

6. The method of claim 5, wherein said optimizing further comprises:
    using the computer to produce a new population of solutions based on said producing offspring;
    using the computer to determine a fitness for said provided new population of solutions based on said at least two fitness functions;
    using the computer to select a new mating pool of solutions from among said new population of solutions, wherein said selecting is based on non-domination of one solution versus another solution;
    using the computer to provide offspring from said selected new mating pool of solutions;
    using the computer to repeat said providing a new population of solutions, determining a fitness for said provided new population, selecting a new mating pool from among said new population, and producing offspring from said selected new mating pool until stopping criteria are met.

7. The method of claim 5, wherein said determining a fitness comprises determining an error in energy prediction and, separately, determining an error in energy gradient prediction using the two or more fitness functions.

8. The method of claim 7, wherein said selecting a mating pool of solutions comprises:
    using the computer to sort each of the solutions from the initialized population based on non-domination to provide a rank;
    using the computer to perform an s-wise tournament selection from the initialized population based on said rank.

9. The method of claim 8, wherein said selecting a mating pool of solutions further comprises:
    for each of the solutions from the initialized population, using the computer to determine a crowding distance;
    wherein said performing an s-wise tournament selection is based on said rank and said crowding distance.

10. The method of claim 1, wherein the accurate method comprises at least one of providing experimental results and inputting the results into the computer, and performing ab initio calculations using the computer.

11. The method of claim 1, further comprising:
    evolving the functional form in the computer using genetic programming (GP).

12. The method of claim 1, further comprising:
    using the computer to simulate chemical reaction dynamics of a molecule based on said optimized functional form.

13. A method for tuning a semiempirical process for predicting energy for different molecular configurations, the method comprising:
    for a first molecule, determining an energy value and an energy gradient for each of a plurality of molecular configurations using an accurate method and providing the energy value and the energy gradient in a computer;
    using the computer to optimize a functional form of the semiempirical process for the first molecule using said determined energy values and energy gradients via a multiobjective optimization, wherein the functional form relates one or more parameters to energy values, and storing the optimal functional form in the computer; and
    using the computer to tune a semiempirical process for predicting energy for different molecular configurations for a second molecule based on said optimized functional form for the first molecule.

14. The method of claim 13, wherein said tuning further comprises:

the computer selecting said optimized functional form for the first molecule from among functional forms for a plurality of different molecules;

the computer tuning a semiempirical process for predicting energy for different molecular configurations for a second molecule based on said selected optimized functional form.

15. The method of claim 13, wherein said second molecule is more complex than said first molecule.

16. The method of claim 2, further comprising:

using the computer to select a subset of the plurality of optimized sets of parameters, wherein said selecting comprises determining a sensitivity of each of the optimized sets of parameters to perturbation.

17. The method of claim 2, further comprising:

for each of at least one of the plurality of optimized sets of parameters, using the computer to determine at least one relationship between one of the parameters in the optimized set and another of the parameters in the optimized set.

18. The method of claim 17, wherein said determining at least one relationship comprises the computer determining a correlation using genetic programming.

19. A computer configured to perform the method of claim 1 comprising:

a processor configured for performing said optimization; and a non-transitory storage medium for storing said optimized functional form.

20. An optimized semiempirical process for predicting energy for different molecular configurations, the process being optimized by a method comprising:

providing a semiempirical process in a computer;

the computer determining an energy value and an energy gradient for each of a plurality of molecular configurations using an accurate method;

the computer optimizing a functional form of the semiempirical process using said determined energy values and energy gradients via multiobjective optimization, wherein the functional form relates one or more parameters to energy values and energy gradients, and storing the optimized functional form in the computer.

21. The method of claim 12, further comprising:

displaying a result of the simulated chemical reaction dynamics on a display coupled to the computer.

* * * * *

UNITED STATES PATENT AND TRADEMARK OFFICE
CERTIFICATE OF CORRECTION

PATENT NO. : 8,301,390 B2
APPLICATION NO. : 12/012502
DATED : October 30, 2012
INVENTOR(S) : Kumara Sastry et al.

It is certified that error appears in the above-identified patent and that said Letters Patent is hereby corrected as shown below:

In the Specification:

Col. 3, line 38    Before "reproduce" please delete "accurate" and insert --accurately-- therefor.

Col. 19, line 30   After "z-score" please delete "score".

Signed and Sealed this
Sixth Day of August, 2013

Teresa Stanek Rea
*Acting Director of the United States Patent and Trademark Office*